United States Patent
Shimizu et al.

(10) Patent No.: US 8,662,668 B2
(45) Date of Patent: Mar. 4, 2014

(54) FUNDUS OCULI OBSERVING DEVICE

(75) Inventors: Hitoshi Shimizu, Tokyo (JP); Takefumi Hayashi, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 246 days.

(21) Appl. No.: 12/991,080

(22) PCT Filed: Mar. 11, 2009

(86) PCT No.: PCT/JP2009/001084
§ 371 (c)(1),
(2), (4) Date: Nov. 4, 2010

(87) PCT Pub. No.: WO2009/141948
PCT Pub. Date: Nov. 26, 2009

(65) Prior Publication Data
US 2011/0051088 A1 Mar. 3, 2011

(30) Foreign Application Priority Data
May 19, 2008 (JP) .................................. 2008-131095

(51) Int. Cl.
A61B 3/14 (2006.01)
A61B 3/00 (2006.01)
A61B 3/10 (2006.01)

(52) U.S. Cl.
USPC ........... 351/206; 351/200; 351/205; 351/211; 351/221

(58) Field of Classification Search
USPC ......... 351/205–206, 200, 211, 246, 221, 212; 600/476, 425
See application file for complete search history.

(56) References Cited

U.S. PATENT DOCUMENTS

| 6,377,349 | B1 | 4/2002 | Fercher | |
|---|---|---|---|---|
| 7,345,770 | B2 | 3/2008 | Chan et al. | |
| 2002/0051512 | A1* | 5/2002 | Toida | 378/21 |
| 2007/0070295 | A1* | 3/2007 | Tsukada et al. | 351/206 |
| 2007/0159597 | A1 | 7/2007 | Fukuma et al. | |
| 2007/0222946 | A1* | 9/2007 | Fukuma et al. | 351/206 |
| 2007/0236660 | A1 | 10/2007 | Fukuma et al. | |
| 2007/0291277 | A1 | 12/2007 | Everett et al. | |
| 2008/0030680 | A1* | 2/2008 | Tsukada et al. | 351/206 |

(Continued)

FOREIGN PATENT DOCUMENTS

| EP | 1201182 A2 | 5/2002 |
|---|---|---|
| EP | 1882445 A2 | 1/2008 |

(Continued)

OTHER PUBLICATIONS

International Search Report for PCT/JP2009/001084; Mail date Jun. 16, 2009.

(Continued)

*Primary Examiner* — Dawayne A Pinkney
(74) *Attorney, Agent, or Firm* — Pearne & Gordon LLP

(57) ABSTRACT

A fundus oculi observing device 1 specifies a characteristic site of a fundus oculi Ef depicted in tomographic images of the fundus oculi Ef and, based on the position of the characteristic site within frames FH and FV of the tomographic images, changes a target position of a signal light LS so that the characteristic site is depicted in the center positions within the frames FH and FV and executes a main measurement, thereby forming a tomographic image and/or a three-dimensional image of the fundus oculi Ef.

11 Claims, 10 Drawing Sheets

(56) References Cited

U.S. PATENT DOCUMENTS

| | | | |
|---|---|---|---|
| 2008/0212028 A1* | 9/2008 | Ichikawa | 351/208 |
| 2010/0110171 A1* | 5/2010 | Satake | 348/78 |
| 2010/0149489 A1* | 6/2010 | Kikawa et al. | 351/206 |

FOREIGN PATENT DOCUMENTS

| | | |
|---|---|---|
| JP | 09-276232 A | 10/1997 |
| JP | 11-325849 A | 11/1999 |
| JP | 2002-139421 A | 5/2002 |
| JP | 2006-153838 A | 6/2006 |
| JP | 2007-024677 A | 2/2007 |
| JP | 2007-185244 A | 7/2007 |
| JP | 2007-275374 A | 10/2007 |
| JP | 2008-073099 A | 4/2008 |
| WO | 2008-142823 A1 | 11/2008 |

OTHER PUBLICATIONS

Extended European Search Report (ESSR); Nov. 2, 2012.

* cited by examiner

FUNDUS OCULI OBSERVING DEVICE

TECHNICAL FIELD

The present invention relates to a fundus oculi observing device that forms a tomographic image of the fundus oculi of an eye.

BACKGROUND ART

In recent years, an optical image measuring technique of forming an image that shows the surface morphology or internal morphology of a measured object by using a light beam from a laser light source or the like has attracted attention. Unlike an X-ray CT apparatus, the optical image measuring technique is noninvasive to human bodies, and is particularly expected to be utilized more in the medical field and biological field.

Patent Document 1 discloses a device to which the optical image measuring technique is applied. This device has a configuration in which: a measuring arm scans an object by a rotary deflection mirror (a Galvano mirror); a reference arm is provided with a reference mirror; and an interferometer is mounted at the outlet to analyze, by a spectrometer, the intensity of the interference light of light fluxes from the measurement arm and reference arm. Besides, the reference arm is configured to gradually change the light flux phase of the reference light by discontinuous values.

The device of Patent Document 1 uses a technique of so-called "Fourier Domain OCT (Optical Coherence Tomography)." That is to say, the device radiates a low-coherence light beam to a measured object, superpose the reflected light and the reference light on each other to generate the interference light, and acquires the spectral intensity distribution of the interference light to execute Fourier transform, thereby imaging the morphology in the depth direction (z-direction) of a measured object.

Furthermore, the device described in Patent Document 1 is provided with a Galvano mirror that scans with a light beam (a signal light), and is thereby configured to form an image of a desired measurement target region of a measured object. Because this device is configured to scan with the light beam only in one direction (x-direction) orthogonal to the z-direction, an image formed by this device is a two-dimensional tomographic image in the depth direction (z-direction) along the scanning direction (x-direction) of the light beam.

Patent Document 2 discloses a technique of scanning with a signal light in the horizontal direction and the vertical direction to form a plurality of two-dimensional tomographic images in the horizontal direction, and acquiring and imaging three-dimensional tomographic information of a measured range based on the plurality of tomographic images. As the three-dimensional imaging, for example, a method of arranging and displaying the plurality of tomographic images in the vertical direction (referred to as stack data or the like), and a method of executing a rendering process on the plurality of tomographic images to form a three-dimensional image are considered.

Patent Documents 3 and 4 disclose other types of OCT devices.

Patent Document 3 describes an OCT device that images the morphology of a measured object by scanning the measured object with lights of various wavelengths, acquiring the spectral intensity distribution based on the interference light obtained by superposing the reflected lights of the lights of the respective wavelengths on the reference light, and executing Fourier transform thereon. Such an OCT device is called Swept Source type or the like.

Further, Patent Document 4 describes an OCT device that radiates a light having a predetermined beam diameter to a measured object and analyzes the components of the interference light obtained by superposing the reflected light and the reference light on each other, thereby forming an image of the measured object in a cross-section orthogonal to the travelling direction of the light. Such an OCT device is called full-field type, en-face type or the like.

Patent Document 5 discloses a configuration in which the OCT technique is applied to the ophthalmologic field. Before the OCT device was applied to the ophthalmologic field, a fundus oculi observing device such as a retinal camera had been used (for example, refer to Patent Document 6).

A fundus oculi observing device using the OCT technique has a merit that an image of a deep part of the fundus oculi can be obtained, when compared with a retinal camera that images the surface of the fundus oculi. Therefore, contribution to increase of the diagnosis accuracy and early detection of a lesion is expected.

Patent Document 1: Japanese Unexamined Patent Application Publication No. 11-325849
Patent Document 2: Japanese Unexamined Patent Application Publication No. 2002-139421
Patent Document 3: Japanese Unexamined Patent Application Publication No. 2007-24677
Patent Document 4: Japanese Unexamined Patent Application Publication No. 2006-153838
Patent Document 5: Japanese Unexamined Patent Application Publication No. 2008-73099
Patent Document 6: Japanese Unexamined Patent Application Publication No. 9-276232

DISCLOSURE OF THE INVENTION

Problem that the Invention is to Solve

However, conventional fundus oculi observing devices to which the OCT device is applied have the following problems. When acquiring tomographic images of the fundus oculi by a conventional fundus oculi observing device, the operator manually performs position matching of a measurement position and, when determining the position matching is completed, manually instructs to start a measurement. To be specific, the operator pushes down a measurement starting button after aligning the scan center of the signal light with the macula center of the fundus oculi.

Since all of the operations including adjustment of a measurement position, determination whether the measurement position is proper and instruction to start a measurement are manually performed as described above, conventional fundus oculi observing devices need a long examination time and place load on subjects and examiners. Moreover, there is a risk that the aforementioned various operations vary among examiners and reproducibility of an examination lowers.

The present invention was made for solving these problems, and an object of the present invention is to provide a fundus oculi observing device that can achieve shortening of an examination time.

Further, another object of the present invention is to provide a fundus oculi observing device that can achieve increase of reproducibility of an examination.

Means for Solving the Problem

In order to achieve the aforementioned objects, a first aspect of the present invention is a fundus oculi observing device comprising: an optical system configured to split a low-coherence light into a signal light and a reference light and make the signal light propagated through a fundus oculi of an eye and the reference light propagated through a reference object interfere with each other to generate an interference light; a detector configured to detect the generated interference light and generate detection signals; a scanner configured to perform a scan of a target position with the signal light on the fundus oculi; an image forming part configured to form a tomographic image of the fundus oculi based on the detection signals generated during the scan; a specifying part configured to specify a characteristic site of the fundus oculi depicted in the formed tomographic image; and a controller configured to, based on a position of the specified characteristic site within a frame of the tomographic image, control the scanner to change the target position of the signal light so that the characteristic site is depicted in a predetermined position within the frame.

A second aspect of the present invention is the fundus oculi observing device according to the first aspect, in which the controller is configured to change the target position of the signal light so that the characteristic site is depicted in a center position of the frame.

A third aspect of the present invention is the fundus oculi observing device according to the first aspect, in which: the scanner is configured to replicate the scan of the target position with the signal light along a predetermined scanning trajectory; the image forming part is configured to, based on the detection signals of the interference light generated from the signal light with which the scan of the target position is replicated, sequentially form the tomographic image of the fundus oculi along the predetermined scanning trajectory; the specifying part is configured to sequentially specify the characteristic site depicted in the sequentially formed tomographic image; and the controller is configured to, based on the position within the frame of the sequentially specified characteristic site, sequentially change the target position of the signal light so that the characteristic site is depicted in the predetermined position.

A fourth aspect of the present invention is the fundus oculi observing device according to the third aspect, in which: the characteristic site is a macula center or optical papilla center of the fundus oculi; the predetermined scanning trajectory includes a plurality of line trajectories arranged radially; the image forming part is configured to, for each of the line trajectories, sequentially form the tomographic image along the line trajectory; the specifying part is configured to, for each of the line trajectories, sequentially specify the characteristic site depicted in the sequentially formed tomographic image along the line trajectory; and the controller is configured to, for each of the line trajectories, based on the position within the frame of the sequentially specified characteristic site, sequentially change the target position of the signal light so that the characteristic site is depicted in the predetermined position.

A fifth aspect of the present invention is the fundus oculi observing device according to the third aspect, in which: the characteristic site is a fundus oculi center between a macula and optical papilla of the fundus oculi; the predetermined scanning trajectory includes a plurality of line trajectories arranged in parallel; the image forming part is configured to, for each of the line trajectories, sequentially form the tomographic image along the line trajectory; the specifying part is configured to, for each of the line trajectories, sequentially specify the characteristic site depicted in the sequentially formed tomographic image along the line trajectory; and the controller is configured to, for each of the line trajectories, based on the position within the frame of the sequentially specified characteristic site, sequentially change the target position of the signal light so that the characteristic site is depicted in the predetermined position.

A sixth aspect of the present invention is the fundus oculi observing device according to the third aspect, in which the controller is configured to obtain a displacement of the position of the specified characteristic site from the predetermined position and change the target position of the signal light based on the obtained displacement.

A seventh aspect of the present invention is the fundus oculi observing device according to the first aspect, in which: the controller includes a determining part configured to determine whether the characteristic site is depicted in the predetermined position; the controller is configured to, when it is determined that the characteristic site is depicted, control the optical system and the scanner to scan the target position of the signal light and generate a new interference light, and control the image forming part to form a new tomographic image based on the new interference light; and the controller is configured to, when it is determined that the characteristic site is not depicted, control the optical system and the scanner to scan the target position with the signal light again and generate a new interference light, control the image forming part to form a new tomographic image based on the new interference light, control the specifying part to specify the characteristic site depicted in the new tomographic image and, based on a position of the specified characteristic site within a frame of the new tomographic image, change the target position of the signal light so that the characteristic site is depicted in a predetermined position within the frame.

An eighth aspect of the present invention is the fundus oculi observing device according to the seventh aspect, in which the determining part is configured to obtain a displacement of the position of the characteristic site from the predetermined position, determine that the characteristic site is depicted in the predetermined position when the obtain displacement is less than a predetermined threshold, and determine that the characteristic site is not depicted in the predetermined position when the displacement is equal to or more than the predetermined threshold.

A ninth aspect of the present invention is the fundus oculi observing device according to the first aspect further comprising a memory configured to store a tomographic image of the fundus oculi of the eye formed in the past, in which: the specifying part is configured to specify the characteristic site depicted in the past tomographic image and the characteristic site depicted in the tomographic image of the fundus oculi newly formed by the image forming part, respectively; and the controller is configured to change the target position of the signal light so that the position of the characteristic site within the frame of the new tomographic image matches the position of the characteristic site within the frame of the past tomographic image.

A tenth aspect of the present invention is the fundus oculi observing device according to the first aspect further comprising a memory configured to store positional information of the characteristic site within a frame of a tomographic image of the fundus oculi of the eye formed in the past, in which: the specifying part is configured to specify the characteristic site depicted in the tomographic image of the fundus oculi newly formed by the image forming part; and the controller is configured to change the target position of the signal light so that the position of the characteristic site within the frame of the new tomographic image matches the position of the characteristic site represented in the positional information.

An eleventh aspect of the present invention is the fundus oculi observing device according to the ninth aspect, in which the controller is configured to obtain a displacement of the position of the new characteristic site from the position of the past characteristic site and change the target position of the signal light based on the obtained displacement.

A twelfth aspect of the present invention is the fundus oculi observing device according to the tenth aspect, in which the controller is configured to obtain a displacement of the position of the new characteristic site from the position of the past characteristic site and change the target position of the signal light based on the obtained displacement.

A thirteenth aspect of the present invention is the fundus oculi observing device according to the first aspect, in which the optical system includes a projector configured to project a fixation target for fixating the eye in a direction corresponding to the characteristic site, to the fundus oculi, and is configured to generate the interference light based on the signal light propagated through the fundus oculi with the fixation target projected.

Effect of the Invention

The fundus oculi observing device according to the present invention functions as an OCT device that forms a tomographic image of the fundus oculi by scanning the target position of a signal light on the fundus oculi. Besides, the fundus oculi observing device according to the present invention acts to specify a characteristic site of the fundus oculi depicted in the formed tomographic image and, based on the position within the frame of the specified characteristic site, control a scanner to change the target position of the signal light so that the characteristic site is depicted in a predetermined position within the frame.

Since the fundus oculi observing device is capable of automatically executing position matching of a measurement position on the fundus oculi, it is possible to achieve shortening of an examination time. Moreover, automation of the position matching of a measurement position makes it possible to repeatedly measure in (almost) the same position on the fundus oculi, and it is possible to achieve increase of reproducibility of an examination.

Figure 1:
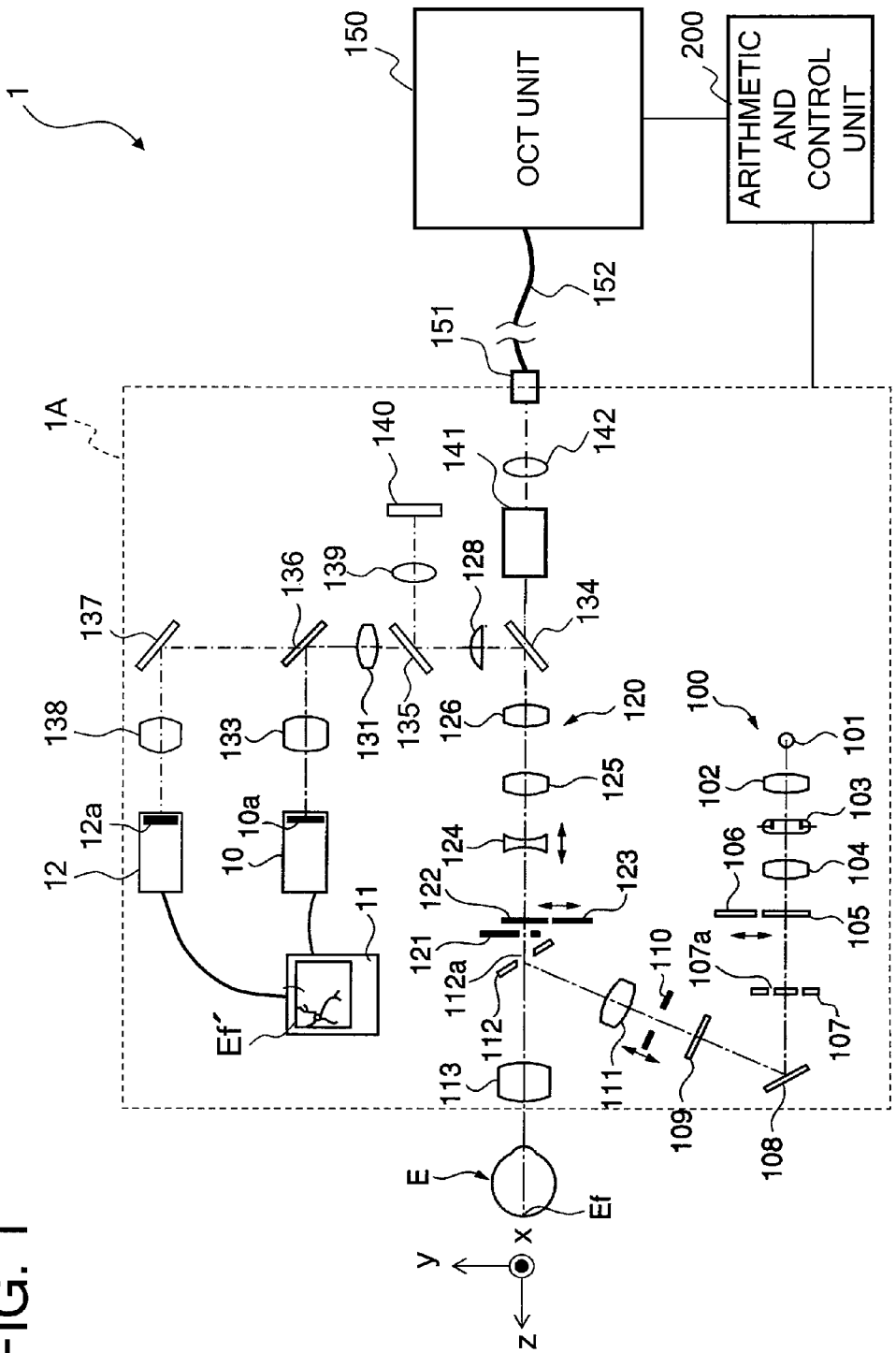
FIG. 1 is a schematic configuration view showing an example of an entire configuration of an embodiment of a fundus oculi observing device according to the present invention.

DESCRIPTION OF REFERENCE NUMERALS AND SYMBOLS 1, 300 fundus oculi observing device
1A retinal camera unit
141 scanning unit
150 OCT unit
160 low-coherence light source
162 optical coupler
174 reference mirror
180 spectrometer
184 CCD
200 arithmetic and control unit
210 controller
211 main controller
212 scan controller
213 memory
214 image position determining part
215 image memory
220 image forming part
230 image processor
231 characteristic site specifying part
240 display part
250 manipulator

BEST MODE FOR CARRYING OUT THE INVENTION

An example of an embodiment of a fundus oculi observing device according to the present invention will be described in detail with reference to the drawings.

The fundus oculi observing device according to the present invention forms a tomographic image of the fundus oculi by the OCT technique. To this fundus oculi observing device, any type of OCT technique, such as Fourier Domain type or Swept Source type, of scanning a target position with a signal light on the fundus oculi is applied. An image acquired by the OCT technique may be referred to as an OCT image.

In this embodiment, a configuration to which a technique of Fourier Domain type is applied will be described in detail. To be specific, this embodiment relates to a fundus oculi observing device having almost the same configuration as the device disclosed in Patent Document 5. In a case that another configuration is applied, it is also possible to obtain similar actions and effects by employing a configuration like that of this embodiment.

<First Embodiment>
[Configuration]

A fundus oculi observing device 1, as shown in FIG. 1, includes a retinal camera unit 1A, an OCT unit 150, and an arithmetic and control unit 200. The retinal camera unit 1A has almost the same optical system as a conventional retinal camera. A retinal camera is a device that photographs the surface of the fundus oculi and acquires a two-dimensional image. Moreover, a retinal camera is utilized for photographing the morphology of fundus oculi blood vessels. The OCT unit 150 houses an optical system for acquiring an OCT image of the fundus oculi. The arithmetic and control unit 200 is provided with a computer that executes various arithmetic processes, control processes, and so on.

To the OCT unit 150, one end of a connection line 152 is attached. To the other end of the connection line 152, a connector part 151 that connects the connection line 152 to the retinal camera unit 1A is attached. An optical fiber 152a runs through inside the connection line 152 (refer to FIG. 2). The OCT unit 150 and the retinal camera unit 1A are optically connected via the connection line 152. The arithmetic and control unit 200 is connected to both the retinal camera unit 1A and the OCT unit 150 via a communication line that transmits electric signals.

[Retinal Camera Unit]

The retinal camera unit 1A has an optical system for forming a two-dimensional image showing the morphology of the surface of the fundus oculi. A two-dimensional image of the surface of the fundus oculi includes images obtained by photographing the surface of the fundus oculi, such as a color image, a monochrome image and a fluorescent image (a fluorescein angiography image, an indocyanine green fluorescent image, and so on).

Like a conventional retinal camera, the retinal camera unit 1A is provided with an illumination optical system 100 and an imaging optical system 120. The illumination optical system 100 radiates an illumination light to a fundus oculi Ef. The imaging optical system 120 leads a fundus oculi reflected light of the illumination light to imaging devices 10 and 12. Moreover, the imaging optical system 120 leads a signal light coming from the OCT unit 150 to the fundus oculi Ef, and also leads the signal light propagated through the fundus oculi Ef to the OCT unit 150.

Like a conventional retinal camera, the illumination optical system 100 includes an observation light source 101, a condenser lens 102, an imaging light source 103, a condenser lens 104, exciter filters 105 and 106, a ring transparent plate 107, a mirror 108, an LCD (Liquid Crystal Display) 109, an illumination diaphragm 110, a relay lens 111, an aperture mirror 112, and an objective lens 113.

The observation light source 101 outputs an illumination light including a wavelength of a visible region in the range from about 400 to 700 nm, for example. The imaging light source 103 outputs an illumination light including a wavelength of a near-infrared region in the range from about 700 to 800 nm, for example. This near-infrared light is set so as to have a shorter wavelength than a light used in the OCT unit 150 (described later).

The illumination light outputted from the observation light source 101 reaches the aperture mirror 112 via the condenser lenses 102 and 104, (the exciter filters 105 and 106,) the ring transparent plate 107, the mirror 108, the LCD 109, the illumination diaphragm 110, and the relay lens 111. Besides, this illumination light is reflected by the aperture mirror 112 to enter an eye E via the objective lens 113 and illuminate the fundus oculi Ef. On the other hand, the illumination light outputted from the imaging light source 103 enters the eye E via a path from the condenser lens 104 to the objective lens 113, and illuminates the fundus oculi Ef.

The imaging optical system 120 includes the objective lens 113, (an aperture 112a of) the aperture mirror 112, an imaging diaphragm 121, barrier filters 122 and 123, a magnifying lens 124, a relay lens 125, an imaging lens 126, a dichroic mirror 134, a field lens 128, a half mirror 135, a relay lens 131, a dichroic mirror 136, an imaging lens 133, the imaging device 10, a reflection mirror 137, an imaging lens 138, the imaging device 12, a lens 139, and an LCD 140. The imaging optical system 120 has almost the same configuration as a conventional retinal camera.

The dichroic mirror 134 reflects the fundus oculi reflected light (having a wavelength included in the range from about 400 to 800 nm) of the illumination light coming from the illumination optical system 100. Moreover, the dichroic mirror 134 transmits a signal light LS (having a wavelength included in the range from about 800 to 900 nm, for example; refer to FIG. 2) coming from the OCT unit 150.

The dichroic mirror 136 transmits the fundus oculi reflected light of the illumination light coming from the observation light source 101. Moreover, the dichroic mirror 136 reflects the fundus oculi reflected light of the illumination light coming from the imaging light source 103.

The LCD 140 displays a fixation target (an internal fixation target) for fixing the eye E. The light from the LCD 140 is focused by the lens 139, reflected by the half mirror 135, propagated through the field lens 128, and reflected by the dichroic mirror 136. Furthermore, this light is propagated through the imaging lens 126, the relay lens 125, the magnifying lens 124, the (aperture 112a of the) aperture mirror 112, the objective lens 113 and so on, and enters the eye E.

Consequently, the internal fixation target is projected to the fundus oculi Ef. The aforementioned optical system for projecting the internal fixation target to the fundus oculi is an example of a "projector" of the present invention.

By changing a position to display the internal fixation target by the LCD 140, it is possible to change a fixation direction of the eye E.

The fixation direction of the eye E is a fixation direction for acquiring an image centered on the macula of the fundus oculi Ef (a fixation direction for macula measurement), a fixation direction for acquiring an image centered on the optic papilla (a fixation direction for papilla measurement), a fixation direction for acquiring an image centered on the fundus oculi center between the macula and the optic papilla (a fixation direction for fundus oculi center measurement), and so on, as in conventional retinal cameras, for example.

The imaging device 10 includes an image pick-up element 10a.

The imaging device 10 is specifically capable of detecting a light of a wavelength in the near-infrared region. In other words, the imaging device 10 functions as an infrared TV camera that detects a near-infrared light. The imaging device 10 detects a near-infrared light and outputs video signals. The image pick-up element 10a is any kind of image pick-up element (area sensor) such as a CCD (Charge Coupled Device) or a CMOS (Complementary Metal Oxide Semiconductor), for example.

The imaging device 12 includes an image pick-up element 12a.

The imaging device 12 is specifically capable of detecting a light of a wavelength in the visible region. In other words, the imaging device 12 functions as a TV camera that detects a visible light. The imaging device 12 detects a visible light and outputs video signals.

Like the image pick-up element 10a, the image pick-up element 12a is composed of any kind of image pick-up element (area sensor).

A touch panel monitor 11 displays a fundus oculi image Ef' based on the video signals from the respective image pick-up elements 10a and 12a. Moreover, the video signals are transmitted to the arithmetic and control unit 200.

The retinal camera unit 1A is provided with a scan unit 141 and a lens 142. The scan unit 141 scans a target position on the fundus oculi Ef with the signal light LS outputted from the OCT unit 150.

The scan unit 141 scans with the signal light LS on the xy-plane shown in FIG. 1. For this purpose, the scan unit 141 is provided with, for example, a Galvano mirror for scanning in the x-direction and a Galvano mirror for scanning in the y-direction.

[OCT Unit]

Figure 2:
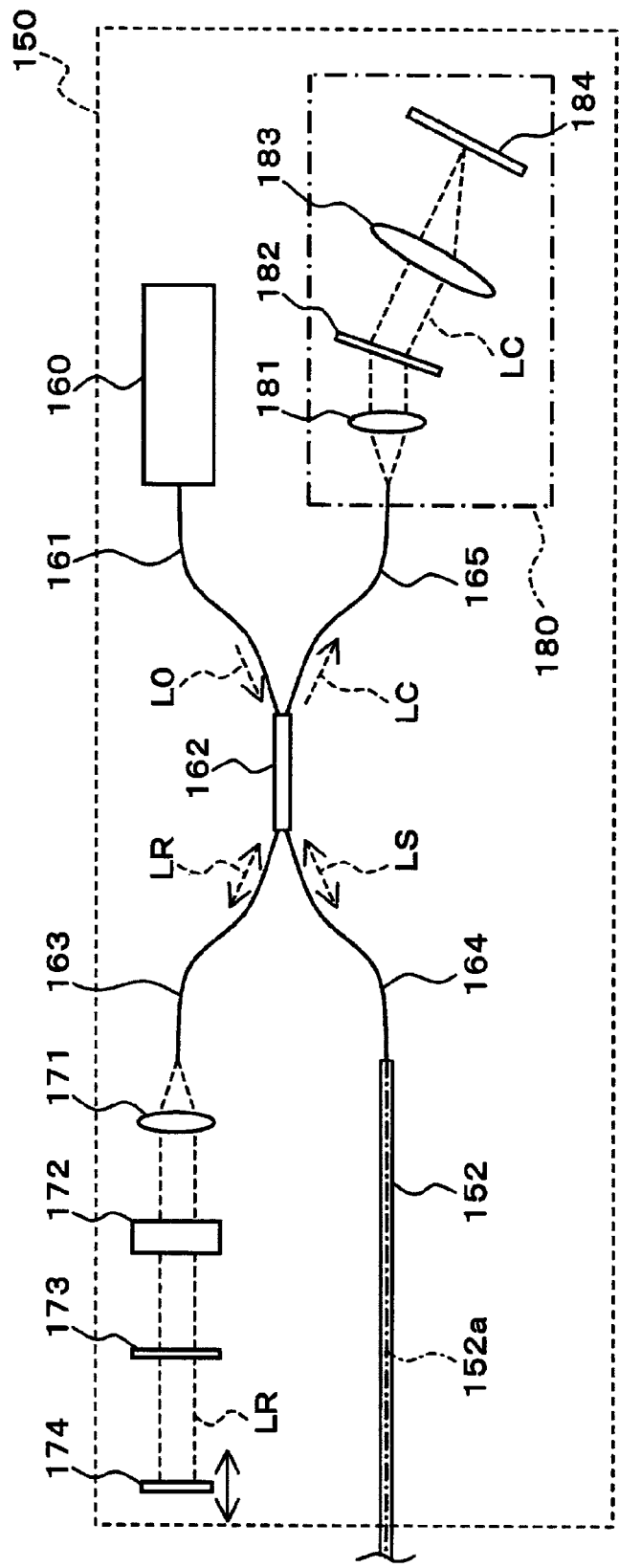
FIG. 2 is a schematic configuration view showing an example of a configuration of an OCT unit in the embodiment of the fundus oculi observing device according to the present invention.

Next, a configuration of the OCT unit 150 will be described with reference to FIG. 2. The OCT unit 150 has an optical system like that of a conventional Fourier-Domain-type OCT device. That is to say, the OCT unit 150 has: an optical system that splits a low-coherence light into a reference light and a signal light and makes the signal light propagated through the fundus oculi of an eye and the reference light propagated through a reference object interfere with each other to generate an interference light; and a detector that detects this interference light. The result of the detection of the interference light (a detection signal) is transmitted to the arithmetic and control unit 200.

A low-coherence light source 160 is a broadband light source that outputs a broadband low-coherence light L0. As this broadband light source, for example, a super luminescent diode (SLD), a light emitting diode (LED) or the like can be used.

For example, the low-coherence light L0 includes a light of a wavelength in the near-infrared region and has a temporal coherence length of about tens of micrometers. The low-coherence light L0 includes a longer wavelength than the illumination light of the retinal camera unit 1A (wavelength of about 400-800 nm), for example, a wavelength in the range from about 800 to 900 nm.

The low-coherence light L0 outputted from the low-coherence light source 160 is led to an optical coupler 162 through an optical fiber 161. The optical fiber 161 is composed of, for example, a single mode fiber, a PM (polarization maintaining) fiber, or the like. The optical coupler 162 splits the low-coherence light L0 into a reference light LR and the signal light LS.

The optical coupler 162 has functions of both a part that splits a light (a splitter) and a part that superposes lights (a coupler), but will be idiomatically referred to as an "optical coupler" herein.

The reference light LR generated by the optical coupler 162 is led by an optical fiber 163 composed of a single mode fiber or the like, and is emitted from the end face of the fiber. Furthermore, the reference light LR is collimated by a collimator lens 171, propagated through a glass block 172 and a density filter 173, and reflected by a reference mirror 174. The reference mirror 174 is an example of a "reference object" of the present invention.

The reference light LR reflected by the reference mirror 174 is again propagated through the density filter 173 and the glass block 172, focused to the fiber end face of the optical fiber 163 by the collimator lens 171, and led to the optical coupler 162 through the optical fiber 163.

The glass block 172 and the density filter 173 act as a delaying part that makes the optical path lengths (the optical distances) of the reference light LR and the signal light LS match each other. Moreover, the glass block 172 and the density filter 173 act as a dispersion compensating part that makes the dispersion properties of the reference light LR and the signal light LS match each other.

The density filter 173 acts as a neutral density filter that reduces the light amount of the reference light LR. The density filter 173 is composed of, for example, a rotary-type ND (Neutral Density) filter. The density filter 173 is driven to rotate by a driving mechanism that is not shown in the drawings, thereby changing the light amount of the reference light LR that contributes to generation of the interference light LD.

Further, the reference mirror 174 is moved in a traveling direction of the reference light LR (a direction of an arrow pointing to both sides shown in FIG. 2) by a driving mechanism that is not shown in the drawings. Thus, it is possible to ensure an optical path length of the reference light LR in accordance with the axial length of the eye E, a working distance (a distance between the objective lens 113 and the eye E), and so on.

On the other hand, the signal light LS generated by the optical coupler 162 is led to the end of the connection line 152 through an optical fiber 164 composed of a single mode fiber or the like. The optical fiber 164 and the optical fiber 152a may be composed of one optical fiber, or may be integrally formed by joining the end faces of the respective fibers.

The signal light LS is led through the optical fiber 152 and guided to the retinal camera unit 1A. Furthermore, the signal light LS is propagated through the lens 142, the scan unit 141, the dichroic mirror 134, the imaging lens 126, the relay lens 125, the magnifying lens 124, the imaging diaphragm 121, the aperture 112a of the aperture mirror 112 and the objective lens 113, radiated to the eye E, and radiated to the fundus oculi Ef. When the signal light LS is radiated to the fundus oculi Ef, the barrier filters 122 and 123 are retracted from the optical path in advance.

The signal light LS having entered the eye E forms an image on the fundus oculi Ef and then is reflected. At this moment, not only the signal light LS is reflected by the surface of the fundus oculi Ef, but also the signal light LS reaches a deep region of the fundus oculi Ef to be scattered at the refractive index boundary. Therefore, the signal light LS propagated through the fundus oculi Ef contains information reflecting the surface morphology of the fundus oculi Ef and information reflecting the state of backscatter at the refractive index boundary of deep layer tissues of the fundus oculi Ef. This light may be simply referred to as a "fundus oculi reflected light of the signal light LS."

The fundus oculi reflected light of the signal light LS is guided reversely on the same path as the signal light LS travelling to the eye E, and focused to the end face of the optical fiber 152a. Besides, the fundus oculi reflected light of the signal light LS enters the OCT unit 150 through the optical fiber 152a, and returns to the optical coupler 162 through the optical fiber 164.

The optical coupler 162 superposes the signal light LS having returned through the fundus oculi Ef and the reference light LR reflected by the reference mirror 174 on each other to generate the interference light LC. This interference light LC is led to a spectrometer 180 through an optical fiber 165 composed of a single mode fiber or the like.

The spectrometer 180 detects the spectral components of the interference light LC. The spectrometer 180 includes a collimator lens 181, a diffraction grating 182, an imaging lens 183, and a CCD 184.

The diffraction grating 182 may be either a transmission-type or a reflection-type. Moreover, it is also possible to use another photodetecting device such as a CMOS, instead of the CCD 184.

The interference light LC having entered the spectrometer 180 is collimated by the collimator lens 181, and divided into spectra by the diffraction grating 182 (spectral resolution). The divided interference lights LC are formed into an image on the image pick-up surface of the CCD 184 by the imaging lens 183. The CCD 184 detects the respective spectral components of the divided interference lights LC and converts the components into electric charges. The CCD 184 accumulates these electric charges and generates detection signals. Furthermore, the CCD 184 transmits the detection signals to the arithmetic and control unit 200. The spectrometer 180 (specifically, the CCD 184) is an example of a "detector" of the present invention.

Although a Michelson-type interferometer is employed in this embodiment, it is possible to employ any type of interferometer such as a Mach-Zehnder-type as necessary.

[Arithmetic and Control Unit]

A configuration of the arithmetic and control unit 200 will be described. The arithmetic and control unit 200 analyzes the detection signals inputted from the CCD 184, and forms an OCT image of the fundus oculi Ef. An arithmetic process therefor is like that of a conventional Fourier-Domain-type OCT device.

Further, the arithmetic and control unit 200 controls each part of the retinal camera unit 1A and OCT unit 150.

As control of the retinal camera unit 1A, the arithmetic and control unit 200 executes: control of output of the illumination lights by the observation light source 101 and the imaging light source 103; control of insertion/retraction of the exciter filters 105, 106 and the barrier filters 122, 123 to/from the optical path; control of the operation of a display device such as the LCD 140; control of movement of the illumination diaphragm 110 (control of the aperture value); control of the aperture value of the imaging diaphragm 121; control of movement of the magnifying lens 124 (control of the magnification); and so on. Furthermore, the arithmetic and control unit 200 controls the scan unit 141 to scan with the signal light LS.

Further, as control of the OCT unit 150, the arithmetic and control unit 200 executes: control of output of the low-coherence light L0 by the low-coherence light source 160; control of movement of the reference mirror 174; control of the rotation operation of the density filter 173 (an operation to change the reduction amount of the light amount of the reference light LR); control of a time for electric charge accumulation, the timing for electric charge accumulation and the timing for signal transmission by the CCD 184; and so on.

The arithmetic and control unit 200 includes a microprocessor, a RAM, a ROM, a hard disk drive, a keyboard, a mouse, a display, a communication interface, and so on, as in conventional computers. The hard disk drive stores a computer program for controlling the fundus oculi observing device 1. Moreover, the arithmetic and control unit 200 may be provided with a circuit board dedicated for forming OCT images based on detection signals from the CCD 184.

[Control System]

Figure 3:
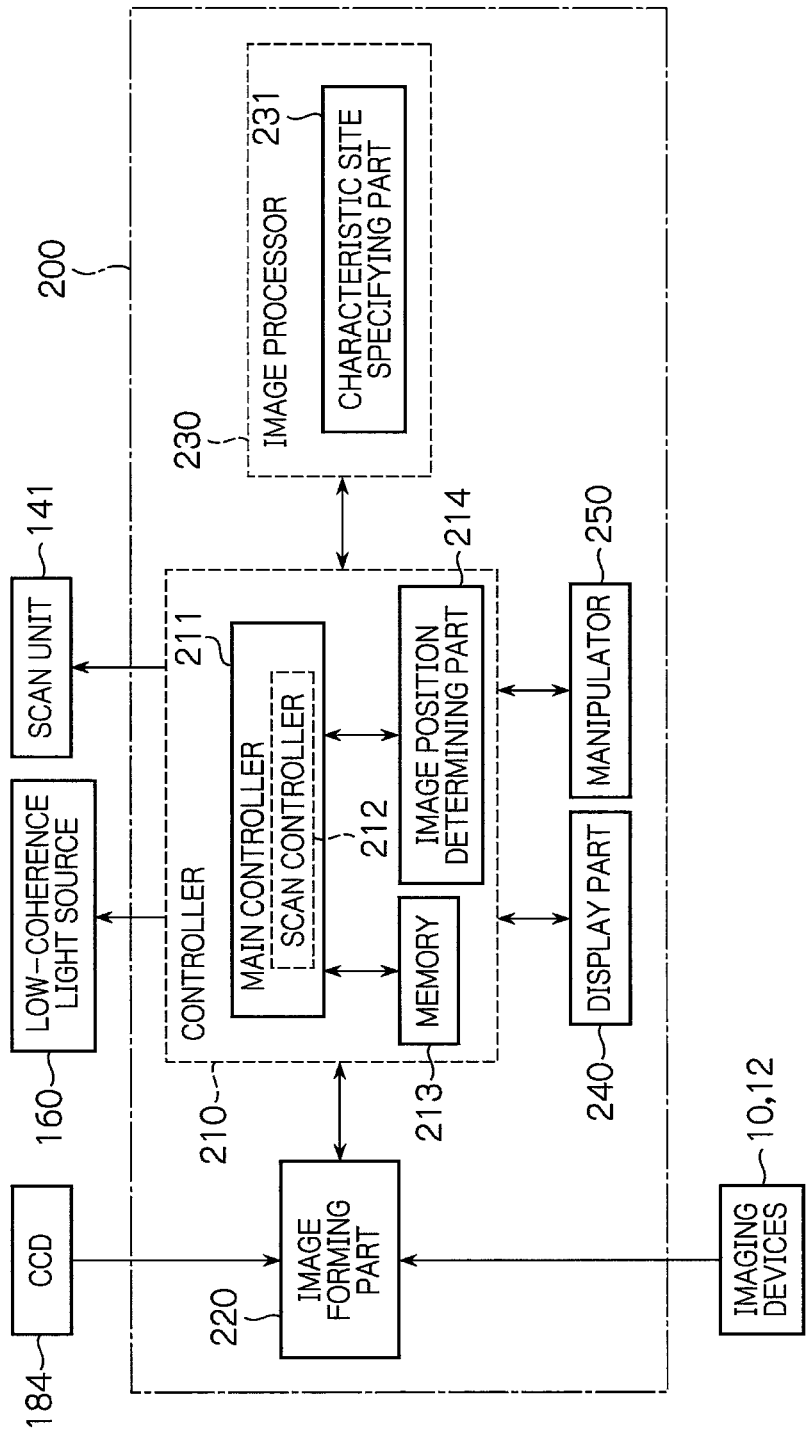
FIG. 3 is a schematic block diagram showing an example of a configuration of a control system of the embodiment of the fundus oculi observing device according to the present invention.

A configuration of a control system of the fundus oculi observing device 1 will be described with reference to FIG. 3.

(Controller)

The control system of the fundus oculi observing device 1 is configured mainly by a controller 210 of the arithmetic and control unit 200. The controller 210 is an example of a "controller" of the present invention. The controller 210 includes, for example, the aforementioned microprocessor, RAM, ROM, hard disk drive, communication interface, and so on.

The controller 210 is provided with a main controller 211. The main controller 211 executes the aforementioned various controls. To be specific, the main controller 211 is provided with a scan controller 212. The scan controller 212 executes a process of setting a scanning aspect of the signal light LS and a control of the scan unit 141. A specific example of an operation of the scan controller 212 will be described later.

Furthermore, the controller 210 is provided with a memory 213. The memory 213 stores various data. The data stored in the memory 213 is, for example, image data of OCT images, image data of the fundus oculi images Ef', eye information, and so on. The eye information includes information on a subject such as a patient ID and a name, and information on an eye such as identification information whether the eye is a left eye or a right eye. Moreover, the memory 213 stores various scanning aspects of the signal light LS. The main controller 211 executes a process of writing data into the memory 213, and a process of reading out data from the memory 213.

Further, the controller 210 is provided with an image position determining part 214. The image position determining part 214 determines whether a characteristic site of the fundus oculi Ef is depicted in a predetermined position of a frame of a tomographic image.

The image position determining part 214 will be described after a characteristic site specifying part 231 of the image processor 230.

The image position determining part 214 is an example of a "determining part" of the present invention.

(Image Forming Part)

An image forming part 220 receives the video signals from the imaging devices 10 and 12 and forms image data of the fundus oculi image Ef'.

Further, the image forming part 220 forms image data of a tomographic image of the fundus oculi Ef based on the detection signals from the CCD 184. Like the conventional Fourier-Domain OCT technique, this process includes processes such as noise elimination (noise reduction), filtering, and FFT (Fast Fourier Transform).

The image forming part 220 includes, for example, the aforementioned circuit board, communication interface and so on. In this specification, "image data" may be identified with an "image" displayed based on the image data.

(Image Processor)

An image processor 230 executes various image processing and analysis processes on the images formed by the image forming part 220.

For example, the image processor 230 executes various correction processes such as luminance correction and dispersion correction of images.

Further, the image processor 230 executes an interpolation process of interpolating pixels between tomographic images formed by the image forming part 220, thereby forming image data of a three-dimensional image of the fundus oculi Ef.

The image data of a three-dimensional image refers to image data that the positions of the pixels are defined by the three-dimensional coordinates. The image data of a three-dimensional image is, for example, image data composed of three-dimensionally arranged voxels. This image data is referred to as volume data, voxel data, or the like. For displaying an image based on the volume data, the image processor 230 executes a rendering process (such as volume rendering and MIP (Maximum Intensity Projection)) on this volume data, and forms the image data of a pseudo three-dimensional image taken from a specific view direction. On a display device such as the display part 240, this pseudo three-dimensional image is displayed.

Further, it is also possible to form stack data of a plurality of tomographic images as the image data of a three-dimensional image.

Stack data is image data obtained by three-dimensionally arranging a plurality of tomographic images obtained along a plurality of scanning lines, based on the positional relation of the scanning lines.

That is to say, stack data is image data obtained by expressing a plurality of tomographic images defined by originally individual two-dimensional coordinate systems by one three-dimensional coordinate system (namely, embedding into a three-dimensional space).

The image processor 230 includes, for example, the aforementioned microprocessor, RAM, ROM, hard disk drive, circuit board, and so on.

The image processor 230 is provided with the characteristic site specifying part 231. The characteristic site specifying part 231 is an example of a "specifying part" of the present invention.

The characteristic site specifying part 231 specifies a characteristic site of the fundus oculi Ef depicted in a tomographic image formed by the image forming part 220. Below, a process example in the case of specifying the macula center of the fundus oculi Ef as a characteristic site will be described. In general, in a tomographic image of the fundus oculi Ef, the macula is depicted as a dent. The characteristic site specifying part 231 specifies the deepest part of the dent as the macula center.

The macula of a healthy eye is expressed as a smoothly curved dent. The characteristic site specifying part 231 firstly specifies an image region (a curved one-dimensional region) corresponding to the fundus oculi surface in a tomographic image of the fundus oculi Ef.

This process is executed by, based on a difference in pixel value (luminance value) between an image region corresponding to the retina and an image region corresponding to the vitreous body in the tomographic image, specifying a boundary region between these image regions, namely, an image region corresponding to the fundus oculi surface. Specification of the boundary region can be realized by, for example, employing known image processing such as threshold processing on pixel values and a boundary extraction process.

After specifying a image region corresponding to the fundus oculi surface (a fundus oculi surface region), the characteristic site specifying part 231 specifies a pixel located in the deepest position (a pixel located in the macula center) from among pixels forming the fundus oculi surface region. This process is executed by, for example, comparing the coordinate values (the z-coordinate values) of the pixels and specifying a pixel having the largest z-coordinate value.

In consideration of a case that the fundus oculi surface region is depicted at a slant in the frame of the tomographic image, it is possible to specify a pixel located in the macula center by detecting an inflection point of a dent of a curve representing the fundus oculi surface region (fit an approximation curve as necessary).

In a case that the eye E is a sick eye, the macula is often depicted as a depression having an irregular shape in the tomographic image of the fundus oculi Ef. In such a case, a depressed part in the fundus oculi surface region is specified by threshold processing or the like as described above, and the center position of the depressed part is specified. This process is executed by specifying the center position of the depressed part in the scanning direction of the signal light LS for acquiring the tomographic image.

In a case that a plurality of tomographic images of the fundus oculi Ef are formed, the characteristic site specifying part 231 specifies a characteristic site in each of the tomographic images. For example, in a case that a cruciform scan or radial scan described later is executed, the characteristic site specifying part 231 specifies a characteristic site depicted in a tomographic image along each of linear trajectories included in the scanning aspect. Besides, in a case that formation of a tomographic image of the fundus oculi Ef is replicated, the characteristic site specifying part 231 specifies a characteristic site in each of the tomographic images formed in a replicated manner.

The characteristic site specifying part 231 transmits positional information of the specified characteristic site, namely, the coordinate values of the characteristic site in the frame of the tomographic image to the controller 210. This positional information is transmitted to the image position determining part 214.

The image position determining part 214 will be described. As described before, the image position determining part 214 determines whether a characteristic site of the fundus oculi Ef is depicted in a predetermined position in the frame of a tomographic image. The image position determining part 214 receives the positional information (the coordinate values) of the characteristic site acquired by the characteristic site specifying part 231, and obtains a displacement of the coordinate values of the characteristic site from the predetermined position in the frame of the tomographic image.

In this embodiment, as the predetermined position of the frame, the center position of the frame (the frame center) will be used. In the frame, a coordinate system is set in advance, and the coordinate values of the frame center are also set in advance. For example, in horizontal scan, a two-dimensional coordinate system set up by the x-axis and the z-axis is set. Besides, in vertical scan, a two-dimensional coordinate system set up by the y-axis and the z-axis is set. The image position determining part 214 obtains a displacement of the coordinates of the characteristic site from the coordinates of the frame center, for example. This displacement is a relative displacement between the two positions and any sort of calculation method may be employed.

Next, the image position determining part 214 determines whether the obtained displacement is less than a predetermined threshold. In a case that the displacement is less than the predetermined threshold, the image position determining part 214 determines that the characteristic site is depicted in the frame center in the tomographic image. On the contrary, in a case that the displacement is equal to or more than the predetermined threshold, the image position determining part 214 determines that the characteristic site is not depicted in the frame center in the tomographic image. As the predetermined threshold described above, any value that represents the allowable range of errors of a depiction position of the characteristic site with respect to the frame center is set in advance. The image position determining part 214 transmits the result of the determination to the main controller 211.

The main controller 211 controls the fundus oculi observing device 1 in accordance with the result of the determination by the image position determining part 214. For example, in the case of determination that the characteristic site is depicted in the frame center, the main controller 211 controls the low-coherence light source 160, the reference mirror 174, the scan unit 141, the CCD 184 and so on to generate a new interference light LC while scanning with the signal light LS. Besides, the main controller 211 controls the image forming part 220 to form a tomographic image of the fundus oculi Ef based on the new interference light LC.

The scanning aspect of the signal light LS for acquiring the new tomographic image (the new scanning aspect) does not need to be the same as the scanning aspect of the signal light LS for acquiring the tomographic image used for the determination process of the depiction position of the characteristic site (the previous scanning aspect). In general, it is desirable that the previous scanning aspect is a relatively simple scanning aspect with emphasis on a measurement speed. On the other hand, it is desirable that the new scanning aspect is a relatively detailed scanning aspect in order to acquire an OCT image used for diagnosis of the fundus oculi Ef. To be specific, a cruciform scan or a radial scan is employed as the previous scanning aspect (a preliminary measurement), and a three-dimensional scan is employed as the new scanning aspect (a main measurement).

On the contrary, in a case that it is determined that the characteristic site is not depicted in the frame center, the main controller 211 (the scan controller 212) changes the target position of the signal light LS on the fundus oculi Ef so that the characteristic site is depicted in the frame center, based on the position of the characteristic site in the frame of the tomographic image. This process is executed in the following manner, for example.

Firstly, the scan controller 212 obtains a displacement of the position of the characteristic site in the frame of the tomographic image of the fundus oculi Ef from the frame center. As this displacement value, the displacement obtained by the image position determining part 214 may be used as it is. In the case of newly obtaining this displacement value, the scan controller 212 executes, for example, a process like the process by the image position determining part 214 described before.

Next, the scan controller 212 changes the target position of the signal light LS on the fundus oculi Ef based on this displacement. This process is executed by, for example, determining a new target position of the signal light LS based on a relation with a displacement of the target position of the signal light LS on the fundus oculi Ef corresponding to a deflection angle of the Galvano mirror of the scan unit 141.

To closely obtain a displacement of the target position of the signal light corresponding to the deflection angle of the Galvano mirror, information of a distance between the objective lens 113 and the fundus oculi Ef is necessary. This information can be obtained based on a distance between the objective lens 113 and the eye E (a working distance) and an axial length of the eye E. The working distance can be acquired by performing position matching (alignment) between the device optical system and the eye E before a measurement, as in conventional ophthalmologic devices. Moreover, it is possible to use the value of a general working distance in the measurement by the fundus oculi observing device 1. Besides, the axial length may be an actual measurement value of the eye E, or may be a standard value of the Gullstrand's eye model or the like.

Further, it is possible to, without referring to such information, previously store a default value of a displacement of the target position of the signal light corresponding to the deflection angle of the Galvano mirror and change the target position of the signal light LS by using the default value. For example, this default value may be set based on clinical data as necessary, or may be theoretically calculated based on a design aspect or the like of the optical system of the fundus oculi observing device 1.

The scan controller 212 controls the scan unit 141 to radiate the signal light LS to the target position after change.

(Display Part and Manipulator)

The display part 240 includes a display. The manipulator 250 includes an input device and manipulation device such as a keyboard and a mouse. The manipulator 250 may include various buttons and keys formed on the housing of the fundus oculi observing device 1 or outside thereof.

The display part 240 and the manipulator 250 do not need to be composed as separate devices. For example, like a touch panel LCD, a device in which the display part 240 and the manipulator 250 are formed in one body can be used.

[Scan with Signal Light and Image Processing]

A scan with the signal light LS and an OCT image will be described.

The scanning aspect of the signal light LS by the fundus oculi observing device 1 is, for example, a horizontal scan, vertical scan, cruciform scan, radial scan, circular scan, concentric scan, helical scan, and so on. These scanning aspects are selectively used as necessary in consideration of an observation site of the fundus oculi, an analysis target (the retinal thickness or the like), a time required to scan, the accuracy of a scan, and so on.

A horizontal scan is a scan with the signal light LS in the horizontal direction (x-direction). The horizontal scan includes an aspect of scanning with the signal light LS along a plurality of scanning lines extending in the horizontal direction arranged in the vertical direction (y-direction). In this aspect, it is possible to set any interval between scanning lines. By setting the interval between scanning lines to be sufficiently narrow, it is possible to form the aforementioned three-dimensional image (three-dimensional scan). A vertical scan is also performed in a similar manner.

A cruciform scan is a scan with the signal light LS along a cruciform trajectory formed by two linear trajectories (line trajectories) orthogonal to each other. A radial scan is a scan with the signal light LS along a radial trajectory formed by a plurality of line trajectories arranged at predetermined angles. The cruciform scan is an example of the radial scan.

A circular scan is a scan with the signal light LS along a circular trajectory. A concentric scan is a scan with the signal light LS along a plurality of circular trajectories arranged concentrically around a predetermined center position. The circular scan is regarded as a special example of the concentric scan. A helical scan is a scan with the signal light LS along a helical trajectory.

With the configuration as described before, the scan unit 141 is capable of scanning with the signal light LS in the x-direction and the y-direction, respectively, and is therefore capable of scanning with the signal light LS along any sort of trajectory on the xy-plane. Thus, it is possible to realize various scanning aspects as described above.

By scanning with the signal light LS in the aspects as described above, it is possible to form a tomographic image in the depth direction (x-direction) along a scanning line (a scanning trajectory).

Moreover, in a case that the interval between scanning lines is narrow, it is possible to form the aforementioned three-dimensional image.

[Operation]

Figure 4:
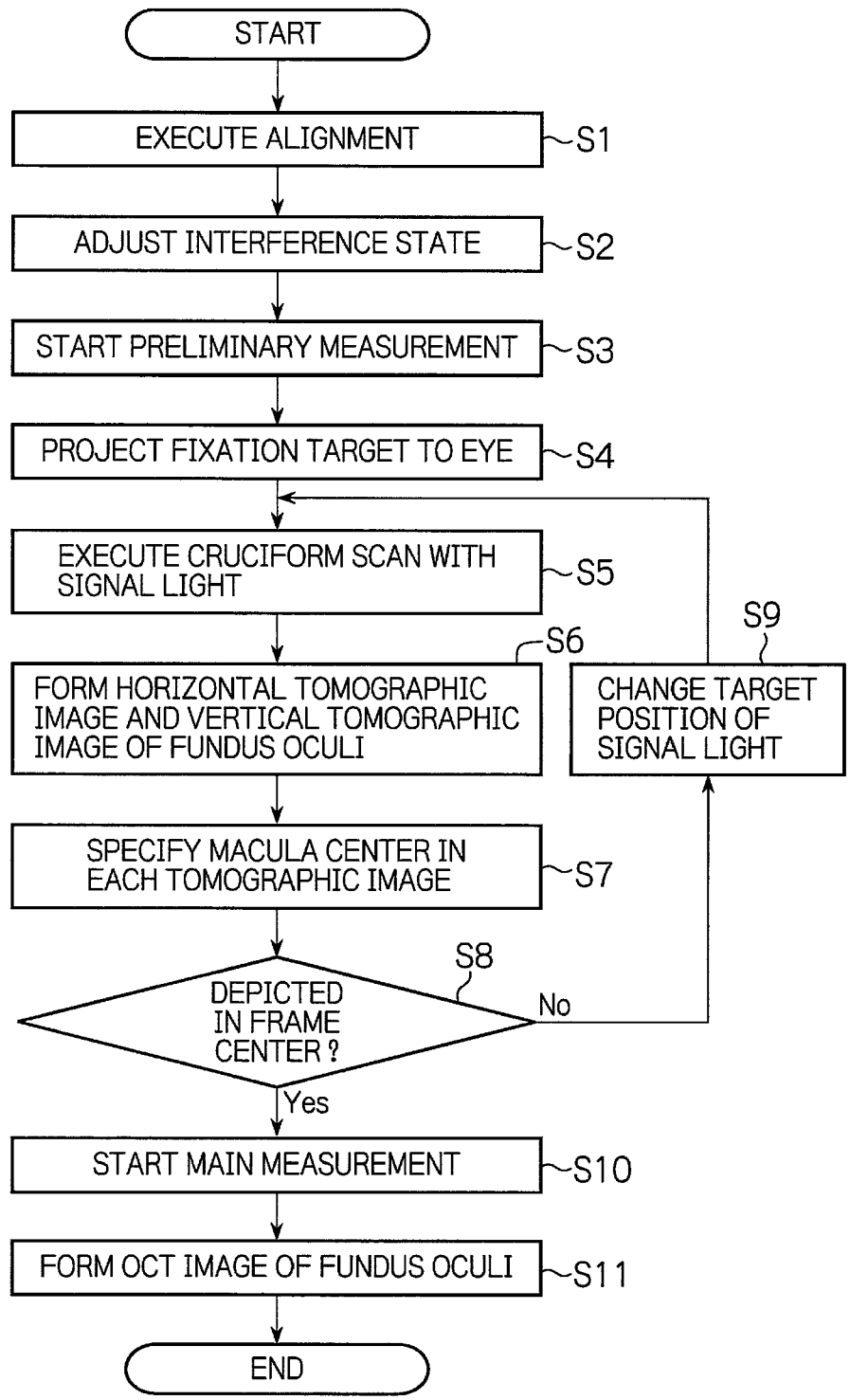
FIG. 4 is a flow chart showing an example of an operation of the embodiment of the fundus oculi observing device according to the present invention.

An operation of the fundus oculi observing device 1 will be described. A flow chart shown in FIG. 4 represents an example of the operation of the fundus oculi observing device 1.

Firstly, alignment of the optical system with respect to the eye E is executed (S1). The alignment is executed in a like manner as in conventional retinal cameras. For example, the alignment is executed by projecting an alignment bright point (not shown) to the eye E and, while observing the state thereof, adjusting the position of the retinal camera unit 1A.

Next, the position of the reference mirror 174 is adjusted, and an interference state between the signal light and the reference light is thereby adjusted (S2). In this case, the adjustment is executed so that an image in a desired depth position of the fundus oculi Ef (for example, the fundus oculi surface) becomes clear. The adjustment of the position of the reference mirror 174 may be manually performed by using the manipulator 250, or may be automatically performed.

When the adjustment of the interference state is completed, a preliminary measurement is started (S3). As mentioned before, the preliminary measurement is a preliminary image measurement for depicting a characteristic site of the fundus oculi Ef in a predetermined position of the frame of a tomographic image. In this embodiment, the preliminary measurement is executed so that the macula center is depicted in the frame center.

The preliminary measurement starts, for example, when the operator performs a predetermined manipulation. Alternatively, the device may be configured to detect the interference state in step S2 and automatically start the preliminary measurement when a favorable interference state is obtained. For example, the device may be configured to monitor the intensity of the interference light in step S2 and start the preliminary measurement when this intensity becomes a predetermined value or more.

When a request to start the preliminary measurement is made, the main controller 211 controls the LCD 140 so that a fixation target is projected to the fundus oculi Ef (S4). At this moment, the operator prompts the subject to stare at the fixation target. A message to prompt the subject to stare at the fixation target may be presented to the subject (display, sound output, or the like). In this operation example, the fixation target is used so as to fixate the eye E in the fixing direction for macula measurement. The operator can manipulate the manipulator 250 to select the fixation direction. Alternatively, the main controller 211 may be configured to automatically select the fixation direction in accordance with the name of injury or disease, the content of examination and so on recorded in the information stored in the memory 213.

Subsequently, by executing control of the output of the low-coherence light L0 by the low-coherence light source 160, control of the scan with the signal light LS by the scan unit 141, control of the operation of the CCD 184, and so on, the main controller 211 generates the interference light LC corresponding to each of the target positions of the signal light LS on the fundus oculi Ef while scanning the target positions, and causes the CCD 184 to detect the spectral components.

The CCD 184 outputs detection signals corresponding to the respective target positions. The image forming part 220 forms tomographic image of the fundus oculi Ef based on these detection signals.

In this operation example, a cruciform scan is employed as the scanning aspect of the signal light LS (S5). As mentioned before, the cruciform scan is a scanning aspect in which a line scan in the horizontal direction (a horizontal scan) and a line scan in the vertical direction (a vertical scan) are combined.

Figure 5:
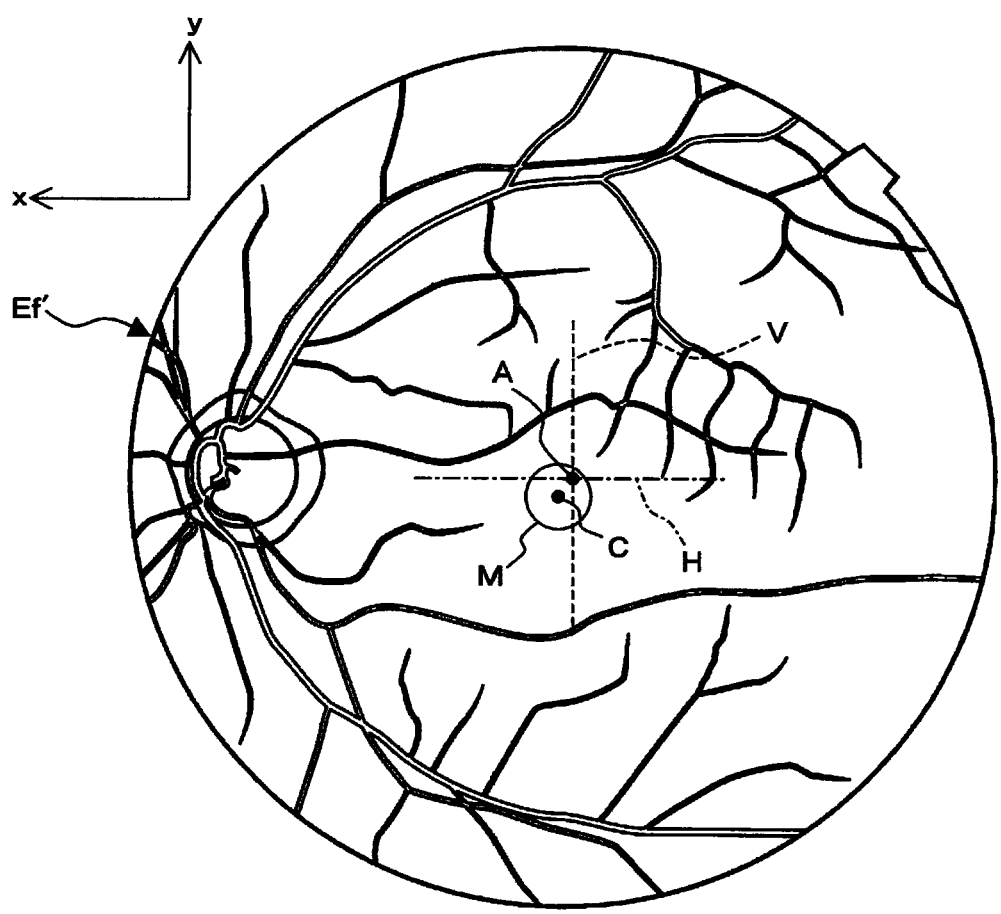
FIG. 5 is a schematic view showing an example of a scanning aspect of a signal light by the embodiment of the fundus oculi observing device according to the present invention.

An example of the cruciform scan is shown in FIG. 5. FIG. 5 shows an observation state of the fundus oculi image Ef'. The cruciform scan includes a horizontal scanning line H and a vertical scanning line V. The intersection of the horizontal scanning line H and the vertical scanning line V (the scan center) is denoted by symbol A.

In the scan state shown in FIG. 5, the scan center A is located off a center (macula center) C of a macula M. That is to say, either the horizontal scanning line H or the vertical scanning line V does not pass through the macula center C. In this operation example, the scanning aspect of the signal light LS is changed so that both the horizontal scanning line H and the vertical scanning line V pass through the macula center C, namely, the scan center A matches the macula center C.

The image forming part 220 forms a tomographic image of a cross section along the horizontal scanning line H (a horizontal tomographic image) and a tomographic image of a cross section along the vertical scanning line V (a vertical tomographic image) based on the detection signals of the interference light LC obtained by cruciform scan of step S5 (S6).

Figure 6A:
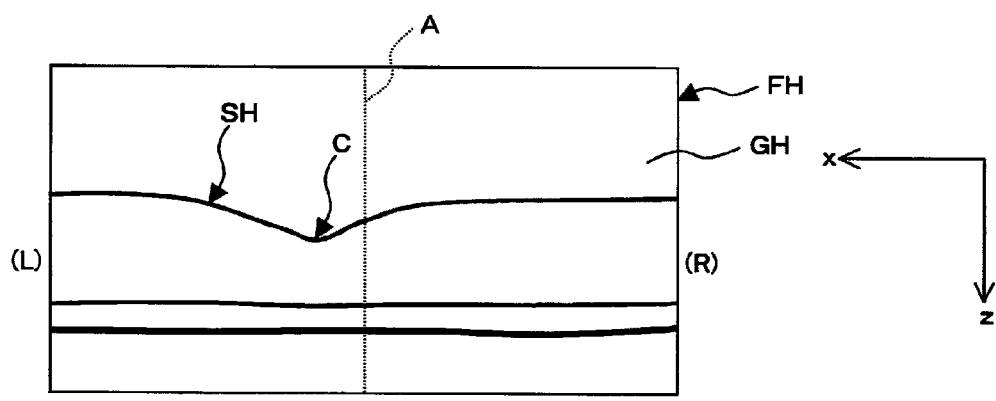
FIGS. 6A and 6B are schematic views showing an example of a tomographic image of the fundus oculi formed by the embodiment of the fundus oculi observing device according to the present invention.
Figure 6B:
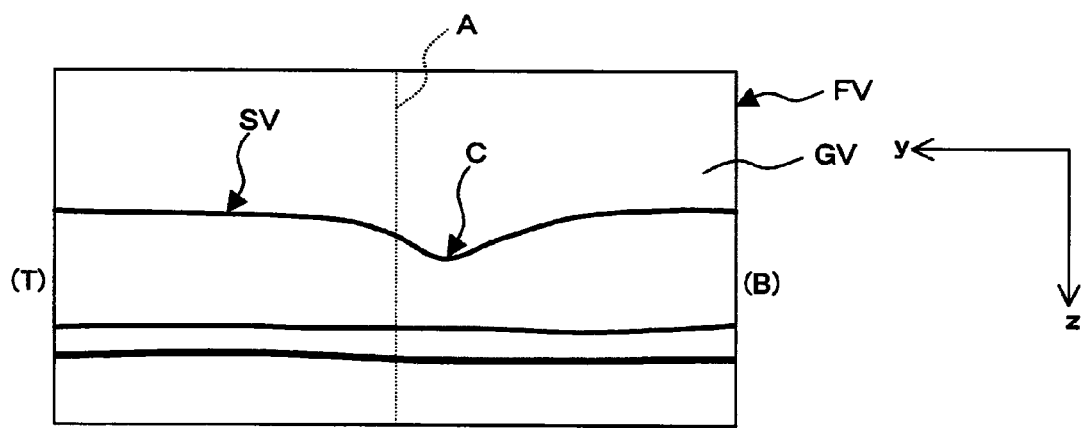

Examples of the two tomographic images obtained by the cruciform scan in FIG. 5 are shown in FIGS. 6A and 6B. FIG. 6A shows a horizontal tomographic image GH along the horizontal scanning line H.

FIG. 6B shows a vertical tomographic image GV along the vertical scanning line V.

The horizontal tomographic image GH is depicted within a frame FH. The frame FH is a two-dimensional image presenting region in which the (R)-(L) direction in the drawing is the horizontal direction (x-direction) and a direction orthogonal thereto is the depth direction (z-direction). The horizontal tomographic image GH includes a fundus oculi surface region SH in which the surface of the fundus oculi Ef is depicted. In the fundus oculi surface region SH, a dent corresponding to the macula M is depicted, and the deepest part of the dent is equivalent to the macula center C. The center position in the x-direction of the frame FH is equivalent to the scan center A. As apparent from a positional relation between the horizontal scanning line H and the macula M (the macula center C) shown in FIG. 5, the macula center C is depicted on the (L)-side from the scan center A.

The vertical tomographic image GV is depicted within a frame FV. The frame FV is a two-dimensional image presenting region in which the (B)-(T) direction in the drawing is the vertical direction (y-direction) and a direction orthogonal thereto is the depth direction (z-direction). The vertical tomographic image GV includes a fundus oculi surface region SV in which the surface of the fundus oculi Ef is depicted. In the fundus oculi surface region SV, a dent corresponding to the macula M is depicted, and the deepest part of the dent is equivalent to the macula center C. The center position in the y-direction of the frame FV is equivalent to the scan center A. As apparent from a positional relation between the vertical scanning line V and the macula M (the macula center C) shown in FIG. 5, the macula center C is depicted on the (B)-side from the scan center A.

The characteristic site specifying part 231 specifies the macula center C depicted in each of the horizontal tomographic image GH and the vertical tomographic image GV (S7). The characteristic site specifying part 231 transmits, to the controller 210, positional information of the macula center C specified from each of the tomographic images GH and GV, namely, the coordinate values of the macula center C in each of the frames FH and FV.

Based on the coordinate values of the macula center C specified in step S7 and the coordinate values of the center position of the frame (the frame center), the image position determining part 214 determines whether the macula center C is depicted in the center position of the frame (S8).

The process in step S8 may be determination whether the macula center C is depicted in the position of the scan center A of each of the frames FH and FV, or may be determination whether the macula center C is depicted in the center of each of the frames FH and FV (namely, the position of the scan center A and the center position in the depth direction z: the center position of a rectangular frame). The "center position of frame" in the present invention shall include at least both the meanings.

For example, as shown in FIGS. 6A and 6B, in a case that it is determined that the macula center C is not depicted in the center position of at least one of the frames FH and FV (S8: No), the scan controller 212 changes the target position of the signal light LS on the fundus oculi Ef based on the coordinate values of the macula center C and the coordinate values of the frame center (including at least the coordinate values of the scan center A) (S9).

Consequently, the scanning aspect is changed so that the macula center C is depicted closer to the frame center than before. Due to movement of the line of sight, involuntary eye movement and so on during a time from the previous scan to the present scan, a slight gap may be made between the frame center and the depiction position of the macula center C in the present scanning aspect. However, by setting the aforementioned predetermined threshold in consideration of such a gap (especially involuntary eye movement and so on) and performing the determination in step S8, it is possible to make the frame center and the depiction position of the macula center C roughly coincide with each other.

The main controller 211 causes the scan unit 141 to execute the cruciform scan while controlling the scan unit 141 to radiate the signal light LS to the target position after change (S5). The image forming part 220 forms a new horizontal tomographic image GH and a new vertical tomographic image GV based on the detection signals of the interference light LC obtained by the new cruciform scan (S6). The characteristic site specifying part 231 specifies the macula center C depicted in each of the new tomographic images GH and GV (S7).

Based on the coordinate values of the macula center C having been newly specified and the coordinate values of the center position of each of the new frames FH and FV, the image position determining part 214 determines whether the macula center C is depicted in the center position of each of the frames FH and FV (S8).

The main controller 211 replicates steps S5-S8 until determination of "Yes" is obtained in step S8. In a case that determination of "Yes" is not obtained in step S8 in spite of replication a predetermined number of times, a measurement of the fundus oculi Ef may be stopped or interrupted and the measurement may be restarted as necessary.

When it is determined that the macula center C is depicted in the center positions of both the frames FH and FV (S8: Yes), a main measurement is automatically started (S10). For this purpose, the scan controller 212 firstly sets a scanning aspect such as a three-dimensional scan. In this case, the scan center in the scanning aspect for main measurement is made to coincide with the scan center at the time of determination of "Yes" in step S8. The main controller 211 controls the low-coherence light source 160, the reference mirror 174, the CCD 184, the scan unit 141 and so on to execute a main measurement.

The image forming part 220 forms a tomographic image of the fundus oculi Ef based on the detection signals of the interference light LC obtained by a main measurement (S11). Moreover, the image processor 230 forms a three-dimensional image of the fundus oculi Ef based on the tomographic images formed by main measurement as necessary. Moreover, the image processor 230 analyzes the tomographic image and the three-dimensional image to obtain the retinal thickness and so on.

Figure 7:
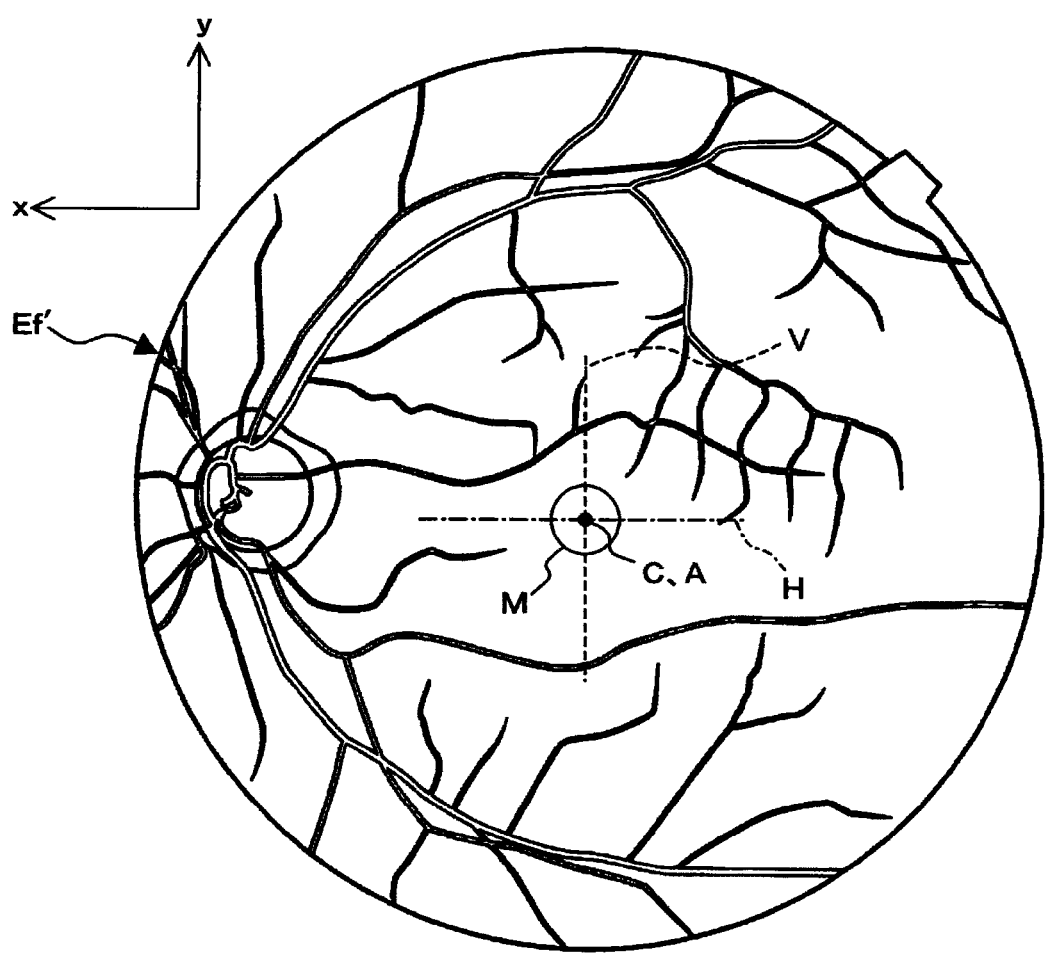
FIG. 7 is a schematic view showing an example of a scanning aspect of a signal light by the embodiment of the fundus oculi observing device according to the present invention.

An example of the scanning state of the signal light LS determined to be "Yes" in step S8 will be described. In this scan state, as shown in FIG. 7, the position of the intersection of the horizontal scanning line H and the vertical scanning line V, namely, the position of the scan center A (substantially) coincides with the position of the macula center C. An error of these positions is within the abovementioned predetermined threshold.

Figure 8A:
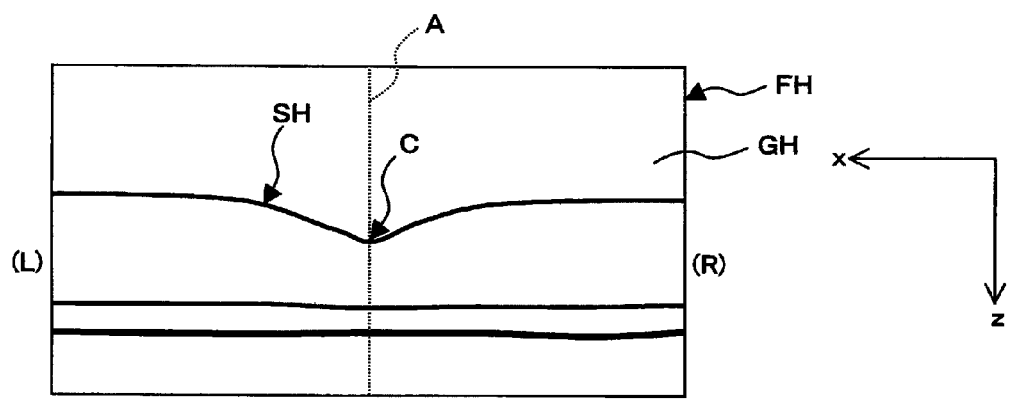
FIGS. 8A and 8B are schematic views showing an example of a tomographic image of the fundus oculi formed by the embodiment of the fundus oculi observing device according to the present invention.
Figure 8B:
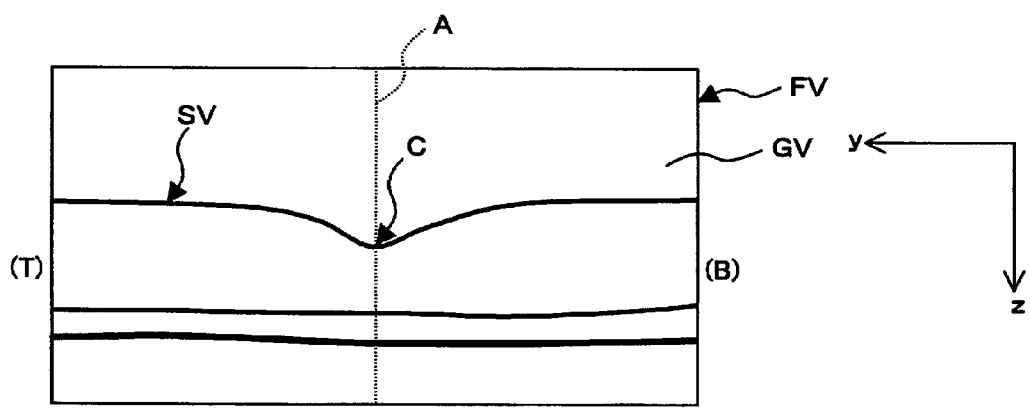

Further, when a scan with the signal light LS is performed in the scanning aspect shown in FIG. 7, a horizontal tomographic image GH and a vertical scanning line V, as shown in FIG. 8A and FIG. 8B, in which the macula center C is depicted in the position of the scan enter A (the frame center) are obtained.

[Actions and Effects]

Actions and effects of the above fundus oculi observing device 1 will be described.

The fundus oculi observing device 1 acts as an OCT device that generates the interference light LC while scanning the fundus oculi Ef with the signal light LS and forms a tomographic image of the fundus oculi Ef based on the detection signals of the interference light LC.

Moreover, the fundus oculi observing device 1 acts so as to specify a characteristic site of the fundus oculi Ef depicted in the tomographic image of the fundus oculi Ef and change the target site of the signal light LS so that the characteristic site is depicted in the center position within each of the frames FH and FV based on the position of the characteristic site within each of the frames FH and FV of the tomographic image.

Since the fundus oculi observing device 1 is capable of automatically executing position matching of a measurement position of the fundus oculi Ef, it is possible to achieve shortening of an examination time. Moreover, since automation of position matching of the measurement position makes it possible to replicate a measurement of (almost) the same position of the fundus oculi Ef, it is possible to achieve increase of reproducibility of an examination.

Further, the fundus oculi observing device 1 replicates a scan of a target position with the signal light LS along a predetermined scanning trajectory, sequentially forms a tomographic image of the fundus oculi Ef along the predetermined scanning trajectory, and sequentially specifies a characteristic site depicted in the tomographic image. Besides, based on the position in each of the frames FH and FV of the sequentially specified characteristic site, the fundus oculi observing device 1 sequentially changes a target position of the signal light LS so that the characteristic site is depicted in the frame center.

By thus replicating the scan, it is possible to adjust a scan position of the signal light LS so that a characteristic site is located in the frame center at all times even in the scan of the eye E that frequently repeats eye movement. That is to say, by thus replicating the scan, it is possible to favorably track a characteristic site.

Further, the fundus oculi observing device 1 has a configuration to project, to the fundus oculi Ef, a fixation target for fixating the eye E in a direction corresponding to a characteristic site, thereby generating the interference light LC based on the signal light LS propagated through the fundus oculi Ef with the fixation target projected. Furthermore, the fundus oculi observing device 1 forms a tomographic image of the fundus oculi Ef based on the detection signals of the interference light LC, and specifies the characteristic site of the fundus oculi Ef depicted in the tomographic image. Then, based on the position of the characteristic site within the frame of the tomographic image, the fundus oculi observing device 1 changes a target position of the signal light LS so that the characteristic site is depicted in a predetermined position within the frame (a frame center).

By thus projecting a fixation target and executing a measurement, it is possible to make a gap between a characteristic site of the fundus oculi Ef and the scan center A small from the beginning, and it is possible to achieve shortening of a time required for position matching of a measurement position. Consequently, it is possible to achieve shortening of an examination time. Specifically in the case of replicating the scan as described above, it is possible to achieve decrease of the number of times of replicating.

Further, the fundus oculi observing device 1 has a configuration to determine whether a characteristic site of the fundus oculi Ef is depicted in a predetermined position within the frame. In the case of determination that the characteristic site is depicted in the predetermined position, the fundus oculi observing device 1 generates a new interference light LC while scanning a target position with the signal light LS, and forms a new tomographic image based on the new interference light.

On the contrary, in the case of determination that the characteristic site is not depicted in the predetermined position, the fundus oculi observing device 1 generates a new interference light LC while scanning a target position with the signal light LS again, and forms a new tomographic image based on the new interference light LC.

Besides, the fundus oculi observing device 1 specifies the characteristic site of the fundus oculi Ef depicted in the new tomographic image and, based on the position of the characteristic site within the frame of the new tomographic image, changes the target position of the signal light LS so that this characteristic site is depicted in the predetermined position within the frame.

According to the fundus oculi observing device 1, a measurement (a main measurement) is automatically executed when a characteristic site of the fundus oculi Ef is depicted in the predetermined position within the frame, and a tomographic image of the fundus oculi Ef is acquired. Consequently, the operator does not need to instruct to start the measurement, and it becomes possible to achieve further shortening of the examination time.

Further, the fundus oculi observing device 1 is configured to, in a case that the characteristic site of the fundus oculi Ef is not depicted in the predetermined position within the frame, execute the process of changing the target position of the signal light LS again so that the characteristic site is depicted in the predetermined position. Thus, since the fundus oculi observing device 1 acts to automatically replicate the process of changing the target position of the signal light LS until a favorable measured position is obtained, it is possible to achieve shortening of an examination time and increase of reproducibility of an examination.

MODIFIED EXAMPLE

The configuration described above is merely an example for favorably implementing the present invention. Therefore, it is possible to make any kind of modification within the scope of the invention as necessary.

In the above embodiment, a case of specifying the macula center C as a characteristic site of the fundus oculi Ef has been described in detail specifically. However, the characteristic site of the fundus oculi Ef is not limited to the macula center C.

For example, it is possible to configure to specify the center of the optic papilla (optical papilla center) of the fundus oculi Ef. Like the macula M, the optical papilla is depicted as a dent on the surface of the fundus oculi. The dent of the optic papilla is generally deeper than that of the macula M. Below, an example of a process of specifying the optical papilla center depicted in a tomographic image of the fundus oculi Ef will be described. Since tracking the optic papilla center by replicating a scan is similar to that of the macula center, a detailed description thereof will be omitted.

Firstly, a fixation target is displayed on the LCD 140, and a fixation target for fixating the eye E in the aforementioned fixation direction for papilla measurement is projected to the fundus oculi Ef. A measurement is performed while a target position of the signal light LS is scanned along a predetermined scanning trajectory in a state that the fixation target is projected to the fundus oculi. Consequently, a tomographic image that passes the optic papilla (or that is around the optic papilla) can be acquired from the beginning. As a scanning aspect in this case, it is possible to employ a cruciform scan or a radial scan as in the case of the macula.

Subsequently, for example, as in the process of specifying the macula center C, the characteristic site specifying part 231 specifies a fundus oculi surface region, and further specifies a pixel that exists in the deepest position (a pixel located in the optic papilla center) from among pixels forming the fundus oculi surface region.

In consideration of a case that the fundus oculi surface region is depicted at a slant in the frame of the tomographic image, it is possible to configure to specify the pixel located in the optic papilla center by detecting an inflection point of a dent of a curve representing the fundus oculi surface region (fit an approximation curve as necessary).

Further, the optic papilla center may be specified in consideration of the shape of the optic papilla. For example, assuming the optic papilla is circular (or elliptical), it is possible to specify two image positions corresponding to the edges of the dent of the optic papilla and regard the position of the bottom of the optic papilla corresponding to the middle position between the two image positions as the optic papilla center.

The fundus oculi observing device according to this modified example, for each of a plurality of line trajectories (the horizontal scanning line, the vertical scanning line, and so on), based on the position within the frame of the sequentially specified optic papilla center, sequentially changes the target position of the signal light LS so that the optic papilla center is depicted in a predetermined position within the frame. This is the end of the description of the case that a specific site of the fundus oculi Ef is the optic papilla center.

It is also possible to specify a fundus oculi center (mentioned before) between the macula and the optic papilla as a characteristic site.

In this case, unlike the process of specifying the macula center, it is desirable to employ a scanning aspect including a plurality of line trajectories arranged in parallel, namely, a scanning aspect including a plurality of horizontal scanning lines (from about several to tens of lines). This is for acquiring a tomographic image in which both the macula and the optic papilla are depicted. Below, an example of a process of specifying the fundus oculi center depicted in a tomographic image of the fundus oculi Ef will be described. Since tracking the fundus oculi center by replicating a scan is similar to tracking of the macula center, a detailed description will be omitted.

Firstly, a fixation target is displayed on the LCD 140, and a fixation target for fixating the eye E in the aforementioned fixation direction for fundus oculi center measurement is projected to the fundus oculi Ef. A measurement is performed while the target position of the signal light LS is scanned by the aforementioned scanning aspect in a state that the fixation target is projected to the fundus oculi.

Consequently, a tomographic image that passes the macula and the optic papilla (or that is around the macula and the optic papilla) can be acquired from the beginning. In this case, a scan with the signal light LS is performed along a plurality of horizontal scanning lines arranged in the vertical direction, so that a plurality of horizontal tomographic images in which the macula and the optic papilla are depicted are obtained.

For example, the characteristic site specifying part 231 specifies a fundus oculi surface region in each of the horizontal tomographic images, and detects two characteristic dents in each of the fundus oculi surface regions. One of the two dents is the macula, and the other is the optic papilla. The characteristic site specifying part 231 identifies the macula and the optic papilla, respectively, as necessary. For example, this process can be performed based on the depths of the dents, or can be performed based on the left/right distinction of the eye E and the direction of the horizontal tomographic image. In a case that, for example, an intermediate position between the macula (macula center) and the optic papilla (center) is set as the fundus oculi center, identification of the macula and the optic papilla is unnecessary.

Subsequently, the characteristic site specifying part 231 specifies the deepest parts of the detected two dents in the fundus oculi surface region as the macula center and the optic papilla center, for example. The macula center and the optic papilla center may be specified by detecting inflection points of two dents of an approximation curve representing the fundus oculi surface region, respectively. It is also possible to specify the macula center and the optic papilla center in consideration of the shapes of the macula and the optic papilla.

Furthermore, the characteristic site specifying part 231 specifies the fundus oculi center depicted in the tomographic image based on the specified macula center and optic papilla center. This process can be performed by specifying a predetermined internally dividing point (a midpoint or the like) of a line segment connecting the macula center and the optic papilla center as the fundus oculi center.

The fundus oculi observing device according to this modified example, for each of a plurality of line trajectories (horizontal scanning lines), based on the position within the frame of the sequentially specified fundus oculi center, sequentially changes the target position of the signal light LS so that the fundus oculi center is depicted in a predetermined position within the frame.

The plurality of line trajectories may include vertical scanning lines and diagonal scanning lines. For example, it is possible to configure to change the target position of the signal light LS by making the position of the intersection of a horizontal scanning line and a first vertical scanning line match the position of the macula center and also making the position of the intersection of the horizontal scanning line and a second vertical scanning line match the position of the optic papilla center. Moreover, it is also possible to configure to form a scanning line of the signal light LS in a predetermined position of the fundus oculi Ef by (automatically, for example) moving a projection position of a fixation target to the fundus oculi Ef. This is the end of the description of the case that a specific site of the fundus oculi Ef is the fundus oculi center.

In the above embodiment, a target position of the signal light LS is changed so that a characteristic site of the fundus oculi Ef is depicted in the center position of the frame of a tomographic image.

However, it is also possible to configure to depict the characteristic site in another position within the frame. For example, it is possible to configure to, in a case that an attention site (a lesion site or the like) other than the characteristic site exists, depict the characteristic site off the frame center so that the attention site is also depicted in the tomographic image. Moreover, in the case of depicting two or more characteristic sites in one tomographic image, it is possible to scan with the signal light LS so that the characteristic sites are depicted in the frame.

<Second Embodiment>

In the first embodiment, a case of replicating a scan with a signal light along a predetermined scanning trajectory has been described specifically in detail. A fundus oculi observing device according to a second embodiment refers to a tomographic image of the fundus oculi of an eye acquired in the past or information obtained from the tomographic image, thereby changing a target position of the signal light in one measurement.

Figure 9:
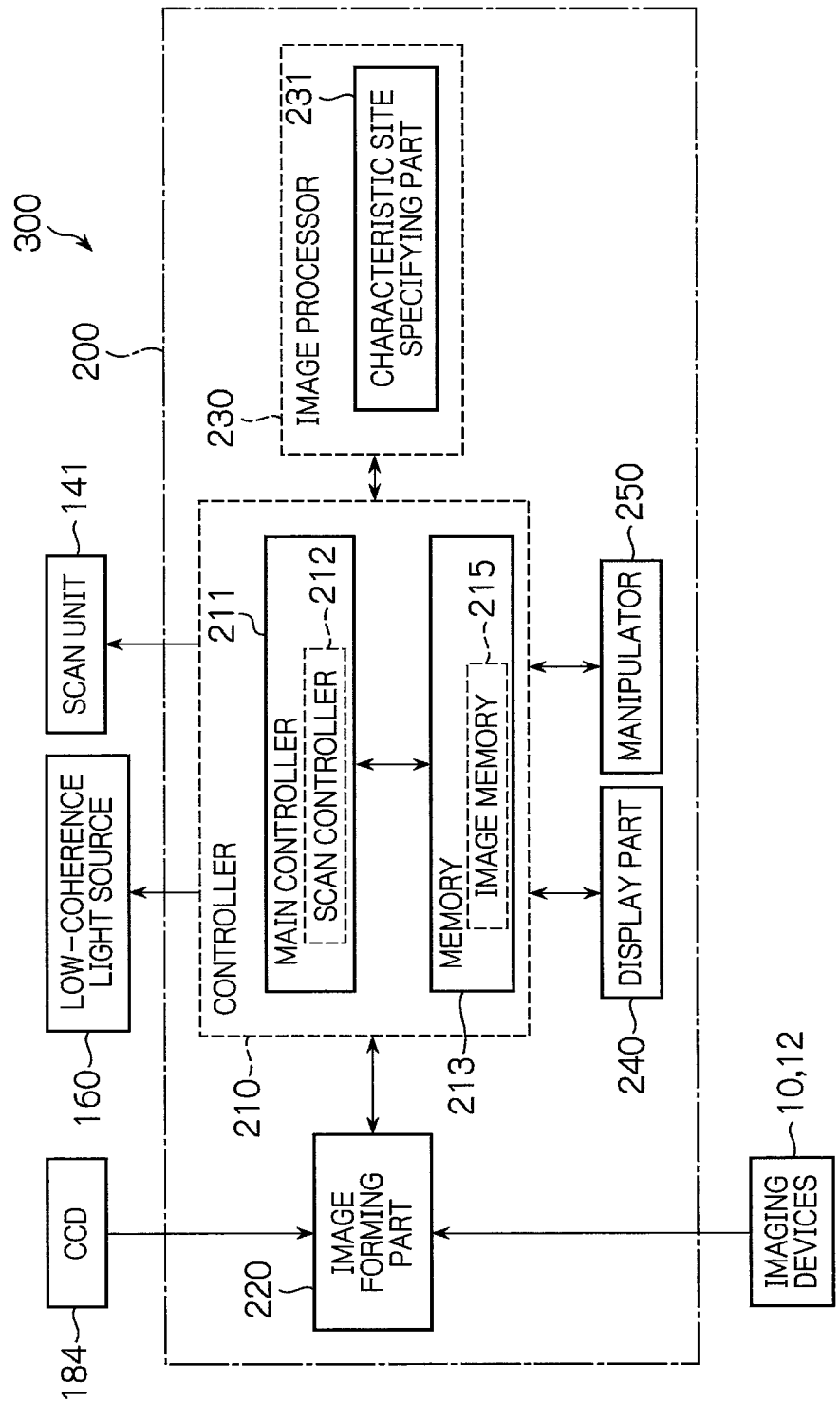
FIG. 9 is a schematic block diagram showing an example of a configuration of the control system of the embodiment of the fundus oculi observing device according to the present invention.

A configuration example of the fundus oculi observing device according to this embodiment is shown in FIG. 9. A fundus oculi observing device 300 has almost the same configuration as the fundus oculi observing device 1 of the first embodiment (refer to FIGS. 1-3).

Below, similar components to those of the first embodiment will be denoted by the same reference numerals.

A memory 213 of the fundus oculi observing device 300 is provided with an image memory 215. The image memory 215 stores an OCT image such as a tomographic image of the fundus oculi acquired in the past (a past image). The past image may be an image acquired by the fundus oculi observing device 300, or may be acquired by another device. The latter past image is inputted into the fundus oculi observing device 300 via any kind of path. For example, the latter past image is stored into an image server on a LAN. The fundus oculi observing device 300 accesses the image server and acquires the past image through the LAN. Moreover, the latter past image is recorded in a recording medium. The fundus oculi observing device 300 reads the past image from the recording medium by a drive device (not shown).

The past image is related to patient information. The patient information includes patient identification information such as a patient ID. The main controller 211 searches for the past image in the image memory 215 based on the patient identification information.

Figure 10:
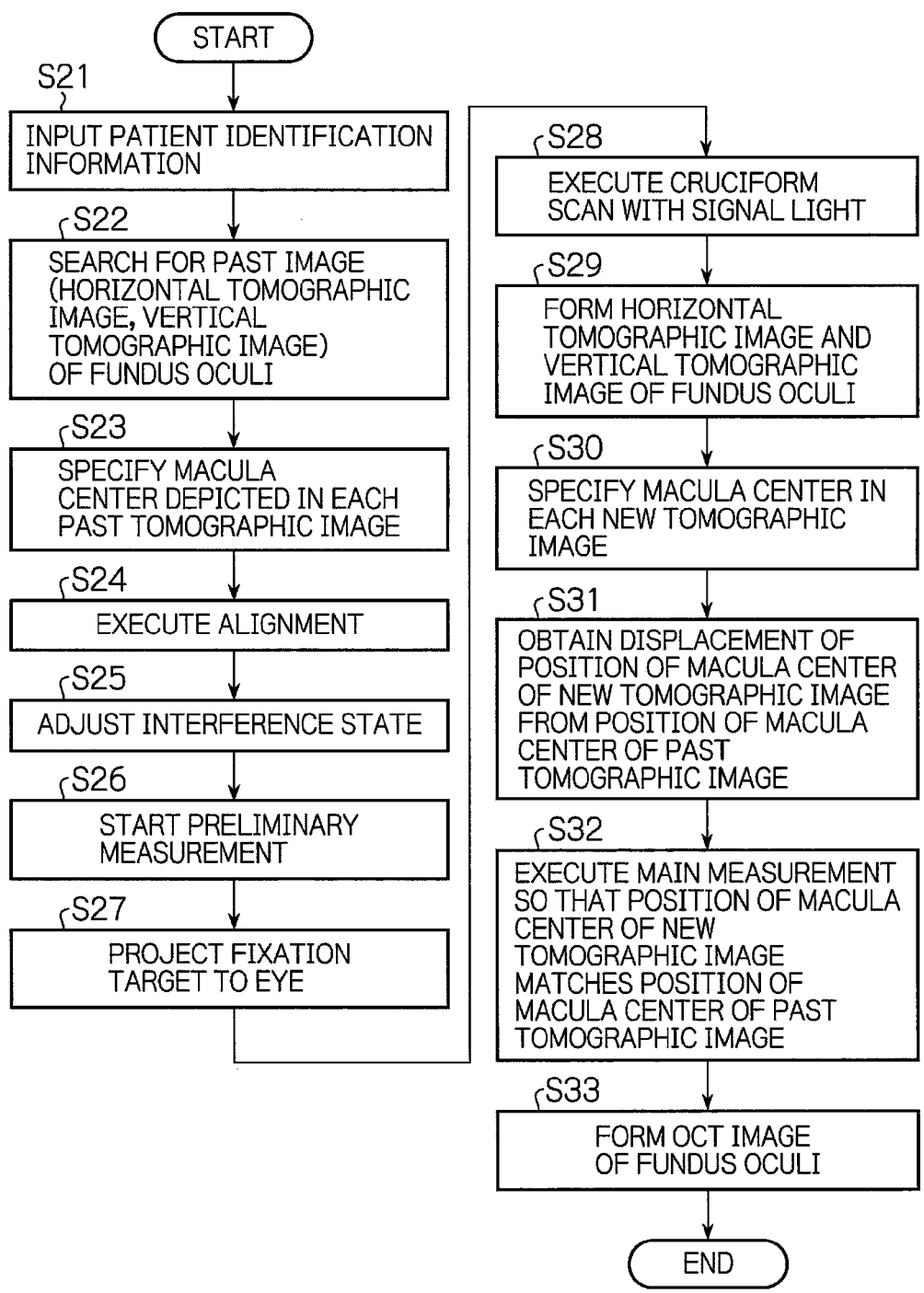
FIG. 10 is a flow chart showing an example of an operation of the embodiment of the fundus oculi observing device according to the present invention.

An operation of the fundus oculi observing device 300 will be described. A flow chart shown in FIG. 10 represents an example of an operation of the fundus oculi observing device 300. In this operation example, the macula center is specified as a characteristic site of the fundus oculi.

Firstly, the operator manipulates the manipulator 250 to input patient identification information of a patient (S21). At this moment, the operator may designate the kind (macula, optic papilla, fundus oculi surface, or the like) of an OCT image to be searched for. Herein, the macula is designated. The main controller 211 searches for a past image (a tomographic image) of the fundus oculi related to the inputted patient identification information in the image memory 215 (S22). Thus, a horizontal tomographic image and vertical tomographic image of the fundus oculi, which have been acquired with the eye fixated in the fixation direction for macula measurement, are searched for. It is possible to configure to display a list of images of the fundus oculi of the eye so that the operator selects and designates a desired image.

The characteristic site specifying part 231 specifies the macula center depicted in each of the horizontal tomographic image and vertical tomographic image having been searched for (S23). Steps S21-S23 may be executed at any timing after that.

Next, as in the first embodiment, alignment of the optical system with respect to the eye is executed (S24), and then adjustment of the position of the reference mirror 174 is executed and adjustment of the interference state between the signal light and the reference light is executed (S25).

When the adjustment of the interference state is completed, a preliminary measurement is started (S26). The main controller 211 controls the LCD 140 so that a fixation target for macular measurement is projected to the fundus oculi (S27). Selection of a fixation target may be automatically performed based on the image type inputted in step S21, or may be manually performed by the operator.

Subsequently, the main controller 211 controls the low-coherence light source 160, the scan unit 141, the CCD 184 and so on to generate the interference light LC while scanning with the signal light LS, and causes the CCD 184 to detect the spectral components.

The CCD 184 outputs detection signals corresponding to the respective target positions of the signal light LS. The image forming part 220 forms a tomographic image of the fundus oculi based on these detection signals.

In this operation example, a cruciform scan is employed (S28).

The image forming part 220 forms a horizontal tomographic image and a vertical tomographic image based on the detection signals of the interference light LC obtained by the cruciform scan (S29).

The characteristic site specifying part 231 specifies the macula center depicted in each of the formed horizontal tomographic image and vertical tomographic image (S30).

Based on the horizontal tomographic image and vertical tomographic image of past images and the new horizontal tomographic image and vertical tomographic image formed in step S29, the scan controller 212 obtains a displacement of the position of the macula center within the frame of the new tomographic image from the position of the macula center within the frame of the past tomographic image, for the horizontal tomographic images and for the vertical tomographic images (S31). This process can be executed by, for example, calculating a displacement of the coordinate values of the macula center in the frame of the new tomographic image from the coordinate values of the macula center in the frame of the past tomographic image.

Based on the displacement obtained in step S31, the main controller 211 executes a main measurement by scanning with the signal light LS so as to make the position of the macula center within the frame of the new tomographic image match the position of the macula center within the frame of the past tomographic image (S32).

The image forming part 220 forms a tomographic image of the fundus oculi based on the detection signals of the interference light LC obtained in the main measurement (S33). Moreover, the image processor 230 forms a three-dimensional image of the fundus oculi based on the tomographic image formed in the main measurement when necessary. Moreover, the image processor 230 analyzes the tomographic image and the three-dimensional image to obtain the retinal thickness or the like. This is the end of the description of the operation.

Actions and effects of the fundus oculi observing device 300 will be described. The fundus oculi observing device 300 acts as an OCT device that generates the interference light LC while scanning the fundus oculi with the signal light LS and forms a tomographic image of the fundus oculi based on the detection signals of the interference light LC. Moreover, the fundus oculi observing device 300 stores a tomographic image of the fundus oculi of the eye formed in the past.

The fundus oculi observing device 300 acts to specify a characteristic site (macula center or the like) of the fundus oculi depicted in the past tomographic image and a characteristic site of the fundus oculi depicted in the newly formed tomographic image, and changes the target position of the signal light LS so as to make the position of the characteristic site within the frame of the new tomographic image match the position of the characteristic site within the frame of the past tomographic image.

Since the fundus oculi observing device 300 is capable of automatically executing position matching of a measurement position of the fundus oculi, it is possible to achieve shortening of an examination time. Moreover, since it is possible to execute a main measurement so as to match a measurement site in a past tomographic image, it is possible to achieve increase of reproducibility of an examination.

Further, the fundus oculi observing device 300 has a configuration to project, to the fundus oculi, a fixation target for fixating an eye in a direction corresponding to a characteristic site, and acts to generate the interference light LC based on the signal light LS propagated through the fundus oculi with the fixation target projected and form a tomographic image of the fundus oculi based on detection signals of the interference light LC. By thus projecting the fixation target and executing a measurement, it is possible to make a gap in measured position between a past image and a present image from the beginning, and it is possible to achieve shortening of a time required for position matching of a measurement position. Consequently, it is possible to achieve shortening of an examination time.

A modified example of the fundus oculi observing device 300 will be described. The fundus oculi observing device 300 described above adjusts a measurement position with reference to a past fundus oculi image of an eye (a past image), whereas a fundus oculi observing device according to the modified example adjusts a measurement position with reference to position information of a characteristic site within the frame of a tomographic image of the fundus oculi of the eye formed in the past.

For this purpose, the fundus oculi observing device according to this modified example stores, in the memory 213, positional information of a characteristic site in the frame of a tomographic image of the fundus oculi formed in the past. The positional information is generated based on the tomographic image of the fundus oculi formed in the past. The positional information includes, for example, the coordinate values of the characteristic site within the frame of the tomographic image formed in the past. The positional information is generated by the aforementioned method by the characteristic site specifying part 231, for example. The positional information may be generated by a like method by another device. In this case, the positional information generated by another device is inputted in the fundus oculi observing device and stored into the memory 213. For example, the positional information is stored in relation with patient identification information and the main controller 211 can search for the positional information based on the patient identification information.

When a tomographic image of the fundus oculi is newly formed by the image forming part 220, the characteristic site specifying part 231 specifies a characteristic site depicted in the new tomographic image. Besides, the main controller 211 changes a target position of the signal light so as to make the position of the characteristic site within the frame of the new tomographic image match the position of the characteristic site represented in the positional information. This process can be executed, for example, as in the fundus oculi observing device 300, by obtaining a displacement of the position of the characteristic site in the new tomographic image (the coordinate values within the frame) from the position of the characteristic site in the past tomographic image (the coordinate values represented in the positional information), and changing the target position of the signal light based on this displacement.

Since the fundus oculi observing device according to this modified example is capable of automatically executing position matching of the measurement position of the fundus oculi, it is possible to achieve shortening of an examination time. Moreover, since it is possible to execute a main measurement so as to match the measurement position of a past tomographic image, it is possible to achieve increase of reproducibility of an examination.

Further, by providing the fundus oculi observing device according to this modified example with a configuration to project, to the fundus oculi, a fixation target for fixating an eye in a direction corresponding to a characteristic site, it is possible to generate the interference light based on the signal light LS propagated through the fundus oculi with the fixation target projected and form a tomographic image of the fundus oculi based on detection signals of the interference light LC. Consequently, it is possible to make a gap in measured position between a past image and a present image small from the beginning, and it is possible to achieve shortening of a time required for position matching of a measurement position and also shortening of an examination time.

Other Modified Examples

Other modified examples of the fundus oculi observing device within the scope of the present invention will be described.

In the first and second embodiments, an OCT device that detects the spectral components of an interference light obtained by radiating a broadband light (a low-coherence light) to the fundus oculi and forms a tomographic image has been described. The present invention can be applied to not only the above type of OCT device but also any type of OCT device provided with a mechanism to scan a target position with the signal light on the fundus oculi. For example, the present invention can be applied to the OCT device of wavelength scanning type (Swept Source type) described in Patent Document 3.

In the aforementioned embodiments, the position of the reference mirror 174 is changed and a difference in optical path length between the optical light of the signal light LS and the optical path length of the reference light LR is changed, but a method for changing the optical path length is not limited thereto. For example, it is possible to change a difference in optical path length by integrally moving the retinal camera unit 1A and the OCT unit 150 with respect to the eye E and changing the optical path length of the signal light LS.

A computer program used in the aforementioned embodiments can be stored in any kind of recording medium that can be read by a drive device of a computer. As this recording medium, for example, an optical disk, a magneto-optic disk (CD-ROM, DVD-RAM, DVD-ROM, MO, and so on), a magnetic storing medium (a hard disk, a floppy disk (TM), ZIP, and so on). Moreover, it is also possible to store into a memory device such as a hard disk drive, memory or the like. Besides, it is possible to transmit/receive this program through a network such as the internet and a LAN.

The invention claimed is:
1. A fundus oculi observing device, comprising:
an optical system configured to split a light from a light source into a signal light and a reference light and make the signal light propagated through a fundus oculi of an eye and the reference light propagated through a reference object interfere with each other to generate an interference light;
a detector configured to detect the generated interference light and generate detection signals;
a scanner configured to perform a scan of a target position with the signal light on the fundus oculi;
an image forming part configured to form a tomographic image of the fundus oculi based on the detection signals generated during the scan;
a specifying part configured to specify a characteristic site of the fundus oculi depicted in the formed tomographic image; and
a controller having a determination part configured to determine a positional relation between the characteristic site of the tomographic image specified by the specifying part and a predetermined position within a frame of the tomographic image, the controller being configured to, based on the determination result, control the scanner to change the target position of the signal light so that the characteristic site is depicted within a standard region from the predetermined position within the frame and to perform another scan of the changed target position with the signal light on the fundus oculi,
wherein the controller is configured to, when it is determined that the characteristic site is depicted within the standard region, control the optical system and the scanner to scan the target position of the signal light and generate a new interference light, and control the image forming part to form a new tomographic image based on the new interference light;
the controller is configured to, when it is determined that the characteristic site is not depicted within the standard region, control the optical system and the scanner to scan the target position with the signal light again and generate a new interference light, control the image forming part to form a new tomographic image based on the new interference light, control the specifying part to specify the characteristic site depicted in the new tomographic image and, based on a position of the specified characteristic site within a frame of the new tomographic image, change the target position of the signal light so that the characteristic site is depicted in a predetermined position within the frame; and
the determining part is configured to obtain a displacement of the position of the characteristic site from the predetermined position, determine that the characteristic site is depicted within the standard region when the obtain displacement is less than a predetermined threshold, and determine that the characteristic site is not depicted within the standard region when the displacement is equal to or more than the predetermined threshold.

2. The fundus oculi observing device according to claim 1, wherein the controller is configured to change the target position of the signal light so that the characteristic site is depicted in a center position of the frame.

3. The fundus oculi observing device according to claim 1, wherein:
the scanner is configured to replicate the scan of the target position with the signal light along a predetermined scanning trajectory;
the image forming part is configured to, based on the detection signals of the interference light generated from the signal light with which the scan of the target position is replicated, sequentially form the tomographic image of the fundus oculi along the predetermined scanning trajectory;

the specifying part is configured to sequentially specify the characteristic site depicted in the sequentially formed tomographic image; and the controller is configured to, based on the position within the frame of the sequentially specified characteristic site, sequentially change the target position of the signal light so that the characteristic site is depicted in the predetermined position.

4. The fundus oculi observing device according to claim 3, wherein:

the characteristic site is a macula center or an optical papilla center of the fundus oculi;

the predetermined scanning trajectory includes a plurality of line trajectories arranged radially;

the image forming part is configured to, for each of the line trajectories, sequentially form the tomographic image along the line trajectory;

the specifying part is configured to, for each of the line trajectories, sequentially specify the characteristic site depicted in the sequentially formed tomographic image along the line trajectory; and the controller is configured to, for each of the line trajectories, based on the position within the frame of the sequentially specified characteristic site, sequentially change the target position of the signal light so that the characteristic site is depicted in the predetermined position.

5. The fundus oculi observing device according to claim 3, wherein:

the characteristic site is a fundus oculi center between a macula and an optical papilla of the fundus oculi;

the predetermined scanning trajectory includes a plurality of line trajectories arranged in parallel;

the image forming part is configured to, for each of the line trajectories, sequentially form the tomographic image along the line trajectory;

the specifying part is configured to, for each of the line trajectories, sequentially specify the characteristic site depicted in the sequentially formed tomographic image along the line trajectory; and the controller is configured to, for each of the line trajectories, based on the position within the frame of the sequentially specified characteristic site, sequentially change the target position of the signal light so that the characteristic site is depicted in the predetermined position.

6. The fundus oculi observing device according to claim 3, wherein the controller is configured to obtain a displacement of the position of the specified characteristic site from the predetermined position and change the target position of the signal light based on the obtained displacement.

7. The fundus oculi observing device according to claim 1, further comprising a memory configured to store a tomographic image of the fundus oculi of the eye formed in the past, wherein:

the specifying part is configured to specify the characteristic site depicted in the past tomographic image and the characteristic site depicted in the tomographic image of the fundus oculi newly formed by the image forming part, respectively;

the standard region is obtained from the position of the characteristic site depicted in the past tomographic image; and the controller is configured to change the target position of the signal light so that the position of the characteristic site within the frame of the new tomographic image matches the position of the characteristic site within the frame of the past tomographic image.

8. The fundus oculi observing device according to claim 1, further comprising a memory configured to store positional information of the characteristic site within a frame of a tomographic image of the fundus oculi of the eye formed in the past, wherein:

the specifying part is configured to specify the characteristic site depicted in the tomographic image of the fundus oculi newly formed by the image forming part; and the controller is configured to change the target position of the signal light so that the position of the characteristic site within the frame of the new tomographic image matches the position of the characteristic site represented in the positional information.

9. The fundus oculi observing device according to claim 7, wherein the controller is configured to obtain a displacement of the position of the new characteristic site from the position of the past characteristic site and change the target position of the signal light based on the obtained displacement.

10. The fundus oculi observing device according to claim 8, wherein the controller is configured to obtain a displacement of the position of the new characteristic site from the position of the past characteristic site and change the target position of the signal light based on the obtained displacement.

11. The fundus oculi observing device according to claim 1, wherein the optical system includes a projector configured to project a fixation target for fixating the eye in a direction corresponding to the characteristic site, to the fundus oculi, and is configured to generate the interference light based on the signal light propagated through the fundus oculi with the fixation target projected.

* * * * *